US009224224B2

(12) United States Patent
Harder et al.

(10) Patent No.: US 9,224,224 B2
(45) Date of Patent: Dec. 29, 2015

(54) METHODS AND SYSTEMS FOR PREDICTIVE CLINICAL PLANNING AND DESIGN AND INTEGRATED EXECUTION SERVICES

(71) Applicants: Donald R Harder, Fishers, IN (US); Daniel D Siders, Westfield, IN (US)

(72) Inventors: Donald R Harder, Fishers, IN (US); Daniel D Siders, Westfield, IN (US)

(73) Assignee: Quintiles Transnational Corporation, Durham, NC (US)

( * ) Notice: Subject to any disclaimer, the term of this patent is extended or adjusted under 35 U.S.C. 154(b) by 119 days.

(21) Appl. No.: 13/925,377

(22) Filed: Jun. 24, 2013

(65) Prior Publication Data

US 2013/0346454 A1 Dec. 26, 2013

Related U.S. Application Data

(60) Provisional application No. 61/663,292, filed on Jun. 22, 2012, provisional application No. 61/663,057, filed on Jun. 22, 2012, provisional application No. 61/663,299, filed on Jun. 22, 2012, provisional application No. 61/663,398, filed on Jun. 22, 2012, provisional application No. 61/663,219, filed on Jun. 22, 2012, provisional application No. 61/663,357, filed on Jun. 22, 2012, provisional application No. 61/663,216, filed on Jun. 22, 2012.

(51) Int. Cl.
*G06F 17/30* (2006.01)
*G06T 11/20* (2006.01)
*G06F 19/00* (2011.01)
*G06F 17/10* (2006.01)

(52) U.S. Cl.
CPC .............. *G06T 11/206* (2013.01); *G06F 17/10* (2013.01); *G06F 17/30292* (2013.01); *G06F 17/30554* (2013.01); *G06F 19/3406* (2013.01); *G06F 19/363* (2013.01)

(58) Field of Classification Search
None
See application file for complete search history.

(56) References Cited

U.S. PATENT DOCUMENTS

| 5,515,488 | A | 5/1996 | Hoppe et al. | |
|---|---|---|---|---|
| 5,966,126 | A | 10/1999 | Szabo | |
| 2003/0065669 | A1* | 4/2003 | Kahn et al. | 707/100 |
| 2003/0108938 | A1* | 6/2003 | Pickar et al. | 435/6 |
| 2004/0093240 | A1* | 5/2004 | Shah | 705/2 |
| 2004/0249664 | A1* | 12/2004 | Broverman et al. | 705/2 |

(Continued)

OTHER PUBLICATIONS

"Present your data in a column chart", Microsoft Office Support for Office Excel 2007, 9 pages.

(Continued)

*Primary Examiner* — Hung Le
(74) *Attorney, Agent, or Firm* — Kilpatrick Townsend & Stockton LLP

(57) ABSTRACT

Systems and methods for predictive clinical planning, design, and integrated execution services are provided. The system may comprise a database, a web server, an application server, and a client.

The system may be used to develop a strategic map of a proposed clinical plan, wherein the clinical plan may include a draft launch label attribute, one or more strategies, and a schema; linking the clinical plan and schema to one or more trials; subsequently linking the trials to one or more objectives and measures; subsequently linking none, one, or a plurality of objectives to none, one, or a plurality of measures; identifying patient criteria and enrolling patients from one or more investigator sites located in one or more countries; and integrating the clinical plan with a clinical plan execution application.

12 Claims, 26 Drawing Sheets

(56) References Cited

U.S. PATENT DOCUMENTS

| | | |
|---|---|---|
| 2005/0182663 A1 | 8/2005 | Abraham-Fuchs et al. |
| 2005/0278286 A1 | 12/2005 | Djugash et al. |
| 2007/0174252 A1 | 7/2007 | Rawlings et al. |
| 2008/0256006 A1* | 10/2008 | Buscema et al. ............... 706/13 |
| 2009/0150351 A1 | 6/2009 | Buck et al. |
| 2009/0240635 A1* | 9/2009 | Qian ............................ 705/500 |
| 2009/0292554 A1 | 11/2009 | Schultz |
| 2009/0299767 A1 | 12/2009 | Michon et al. |
| 2009/0313048 A1* | 12/2009 | Kahn et al. ...................... 705/3 |
| 2010/0088245 A1* | 4/2010 | Harrison et al. ............. 705/317 |
| 2010/0185399 A1* | 7/2010 | Slotman .......................... 702/19 |
| 2010/0274495 A1* | 10/2010 | Sobol ............................. 702/19 |
| 2010/0280975 A1* | 11/2010 | Wischik et al. ............. 705/500 |
| 2011/0238438 A1 | 9/2011 | Houriet, Jr. et al. |
| 2011/0307267 A1* | 12/2011 | Young et al. ..................... 705/2 |
| 2012/0221553 A1 | 8/2012 | Wittmer et al. |
| 2013/0216524 A1* | 8/2013 | Ricci et al. ................. 424/133.1 |
| 2013/0342542 A1 | 12/2013 | Brant et al. |
| 2013/0346093 A1 | 12/2013 | Goodgame et al. |
| 2013/0346094 A1 | 12/2013 | Goodgame et al. |
| 2013/0346111 A1 | 12/2013 | Goodgame |
| 2013/0346454 A1* | 12/2013 | Harder et al. ................. 707/812 |

OTHER PUBLICATIONS

U.S. Appl. No. 13/925,187, Non-Final Office Action, mailed Apr. 15, 2015, 16 pages.

U.S. Appl. No. 13/925,212, Non-Final Office Action, mailed Jun. 4, 2015, 18 pages.

U.S. Appl. No. 13/925,229, Non-Final Office Action, mailed Mar. 17, 2015, 17 pages.

U.S. Appl. No. 13/925,262, Non-Final Office Action, mailed Apr. 23, 2015, 24 pages.

Rafi, "How to Create Overlapping Bars Chart", https://social.msdn.microsoft.com/forums/vstudio/en-US/a2d0b018-7bf3-4d8f-8914-7956de6da7d2/how-to-create-overlapping-bars-chart, Apr. 12, 2012, 4 pages.

* cited by examiner

Objective Associator – EQ-5D

⊞ Primary Objectives
☐ 1  To compare different dosing schedules of BIL non-inferiority of HbA1c after 4 months of therapy in T1DM patients; non-inferiority margin (NIM) = 0.4%

⊞ Secondary Objectives
☐ 1  Total and nocturnal hypoglycemia rate
☐ 2  FBG-absolute and change from baseline
☐ 3  FBG-intra-subject variability
☐ 4  SMBG (9-point) same problem as above, training point during ISST, multiple time points?
☐ 5  Weight change from baseline
☐ 6  HbA1c change from baseline
☐ 7  Proportion of patients with HbA1c < 7.0%
☐ 8  LY antibodies
☐ 9  Additional safety endpoints
☐ 10 Pharmacokinetics ⊞ Exploratory Objectives

FIG. 10

New enrollment model

| | | | | | | | |
|---|---|---|---|---|---|---|---|
| | I2R-MC_BIAO-C2 (BIAO Team update 150ex2010) | | | | | | |

Site Start-Up | Enrollment | Milestones | Time-To-Event | Country Summary

« Actual Investigator Sites By Date

◉ None

« Enrollment Parameters

Desired # Of Patients  [1113]
Max Duration (mo) [36]
Site Rejection % [0]
Pts/Mo Variance % [0]
Historical Patients [ ▼ ]

» Quick Rules  ⊖ ⊕

» New Investigator Site

» Time-To-Event Parameters

» Required Patient Rules

» Site ▣ ⤢

No Site

| Country | | | | | | | |
|---|---|---|---|---|---|---|---|
| ✓ | ○ Investigator Site | ○ | Country | SSU | +/- SSU | Pts/Mo | +/- Pts/Mo |
| ▸ Country: AUSTRALIA (33 of 33 items) | | | | | | | |
| ▸ Country: AUSTRIA (13 of 13 items) | | | | | | | |
| ▾ Country: BELGIUM (20 of 20 items) | | | | | | | |
| ☐ | 1175831 | ⊚ | BELGIUM | 62 | 83.0 | 0.5 | 0.7 |
| ☐ | 1178111 | ⊚ | BELGIUM | 236 | 63.0 | 1.2 | 0.7 |
| ☐ | 1014228 | ⊚ | BELGIUM | 223 | 50.2 | 1.0 | 0.0 |
| ☐ | 1189615 | ⊚ | BELGIUM | 178 | 63.0 | 0.8 | 0.7 |

METHODS AND SYSTEMS FOR PREDICTIVE CLINICAL PLANNING AND DESIGN AND INTEGRATED EXECUTION SERVICES

REFERENCE TO RELATED APPLICATIONS

This application claims priority to U.S. Provisional Application No. 61/663,292, filed on Jun. 22, 2012, entitled "Method and System to Manipulate Multiple Selections against a Population of Elements;" U.S. Provisional Application No. 61/663,057, filed on Jun. 22, 2012, entitled "Systems and Methods For Predictive Analytics For Site Initiation and Patient Enrollment;" U.S. Provisional Application No. 61/663,299, filed on Jun. 22, 2012, entitled "Methods and Systems for Predictive Clinical Planning and Design and Integrated Execution Services;" U.S. Provisional Application No. 61/663,398, filed on Jun. 22, 2012, entitled "Systems and Methods for Subject Identification (ID) Modeling;" U.S. Provisional Application No. 61/663,219, filed Jun. 22, 2012, entitled "Systems and Methods for Analytics on Viable Patient Populations;" U.S. Provisional Application No. 61/663,357, filed Jun. 22, 2012; entitled "Methods and Systems for a Clinical Trial Development Platform;" U.S. Provisional Application No. 61/663,216, filed Jun. 22, 2012; entitled "Systems and Methods for Data Visualization." The entirety of all of which is hereby incorporated by reference herein.

FIELD OF THE INVENTION

Embodiments of the disclosure relate generally to planning, designing, and executing clinical trials. More particularly, embodiments of the disclosure relate to methods and systems for providing predictive clinical planning, design, and integrated execution services used in the research and development of pharmaceuticals.

BACKGROUND

A clinical trial is an extremely complicated undertaking. The process normally involves multiple iterations of each stage in the planning, design, execution, and analysis cycle for pharmaceutical development because negative data about the safety or efficacy of the pharmaceutical product will require reformulation, which will then necessitate subsequent small scale trials before larger trials may be attempted.

Before beginning a clinical trial, a significant amount of time and effort is spent in designing the trial. Due to the effort and expense of conducting the trial, it is critical that the trial be designed to be as effective and efficient as possible. This involves gathering and analyzing a large amount of information. Prior art systems attempted to deal with this problem by maintaining information regarding the design of a trial in a multiplicity of documents, such as spreadsheets and word processing documents. However, this approach had problems. For example, if information was captured in one source and needed to be transferred to another source, this had to be done manually. This led to wasted effort, expense, and increased opportunities for errors.

SUMMARY

Embodiments of the disclosure provide systems and methods for predictive clinical planning, design, and integrated execution services. In one embodiment, the system comprises a database, a web server that facilities entry and retrieval of data between the database and the user, an application server that displays and accepts information to and from one or more users, and a client that is used to display information to users and to receive input from users.

In another embodiment, one or more users develop a strategic map of a proposed clinical plan, wherein the clinical plan includes a draft launch label attribute, one or more strategies, and a schema; linking the clinical plan and schema to one or more trials; subsequently linking the trials to one or more objectives and measures; subsequently linking none, one, or a plurality of objectives to none, one, or a plurality of measures; identifying patient criteria and enrolling patients from one or more investigator sites located in one or more countries; and integrating the clinical plan with a clinical plan execution application.

These embodiments are mentioned not to limit or define the disclosure, but to provide examples to aid understanding thereof. Embodiments are discussed in the Detailed Description, and further description is provided there. Advantages offered by the various embodiments may be further understood by examining this specification.

BRIEF DESCRIPTION OF THE DRAWINGS

These and other features, aspects, and advantages of the present disclosure are better understood when the following Detailed Description is read with reference to the accompanying drawings, wherein:

FIG. 10 is a diagram illustrating an objectives associator according to one embodiment;

FIG. 17 is a diagram illustrating an enrollment editor according to one embodiment;

Figure 18:
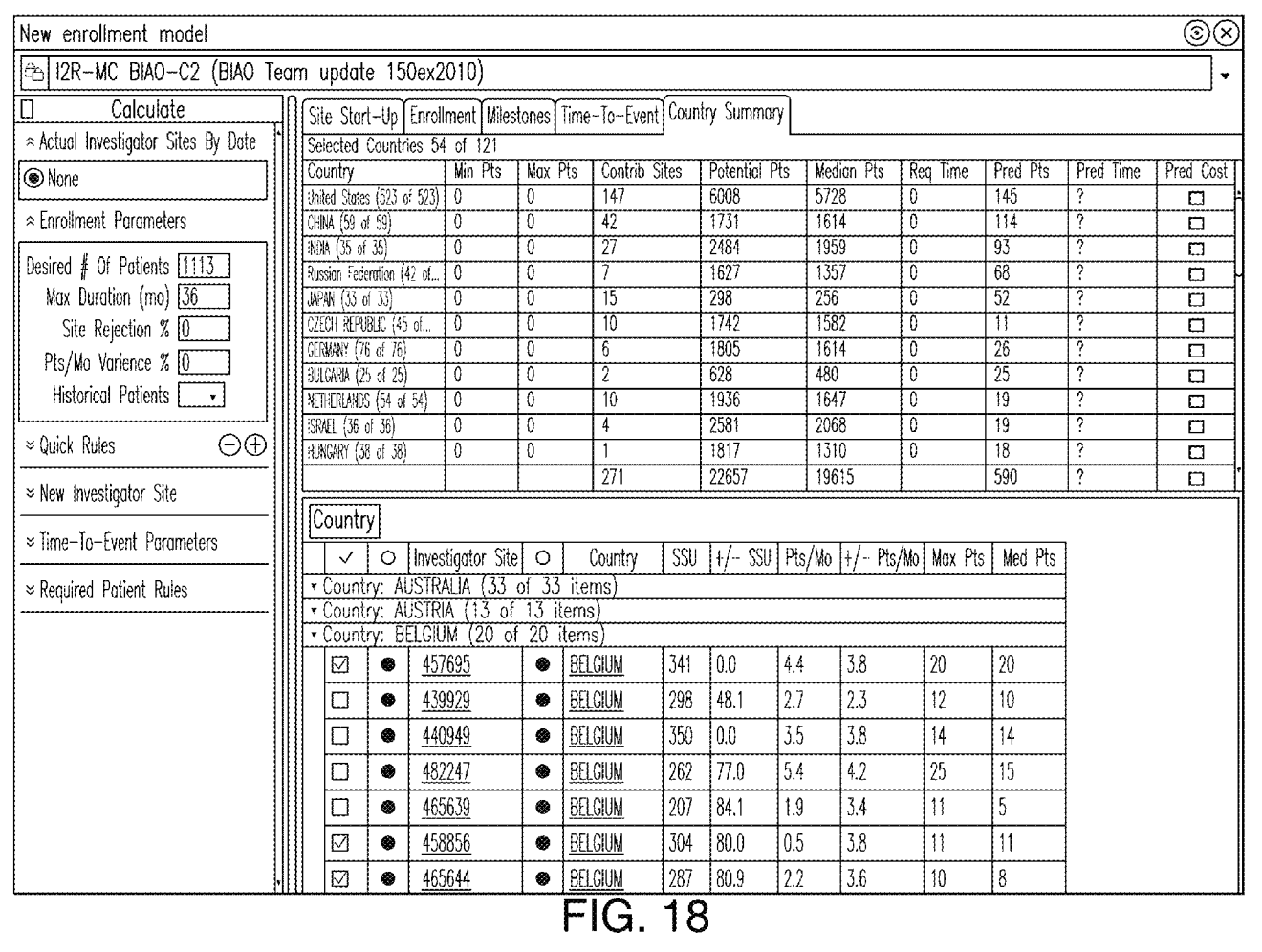

FIG. 18 is a diagram illustrating an enrollment editor according to one embodiment;

DETAILED DESCRIPTION

Figure 1:
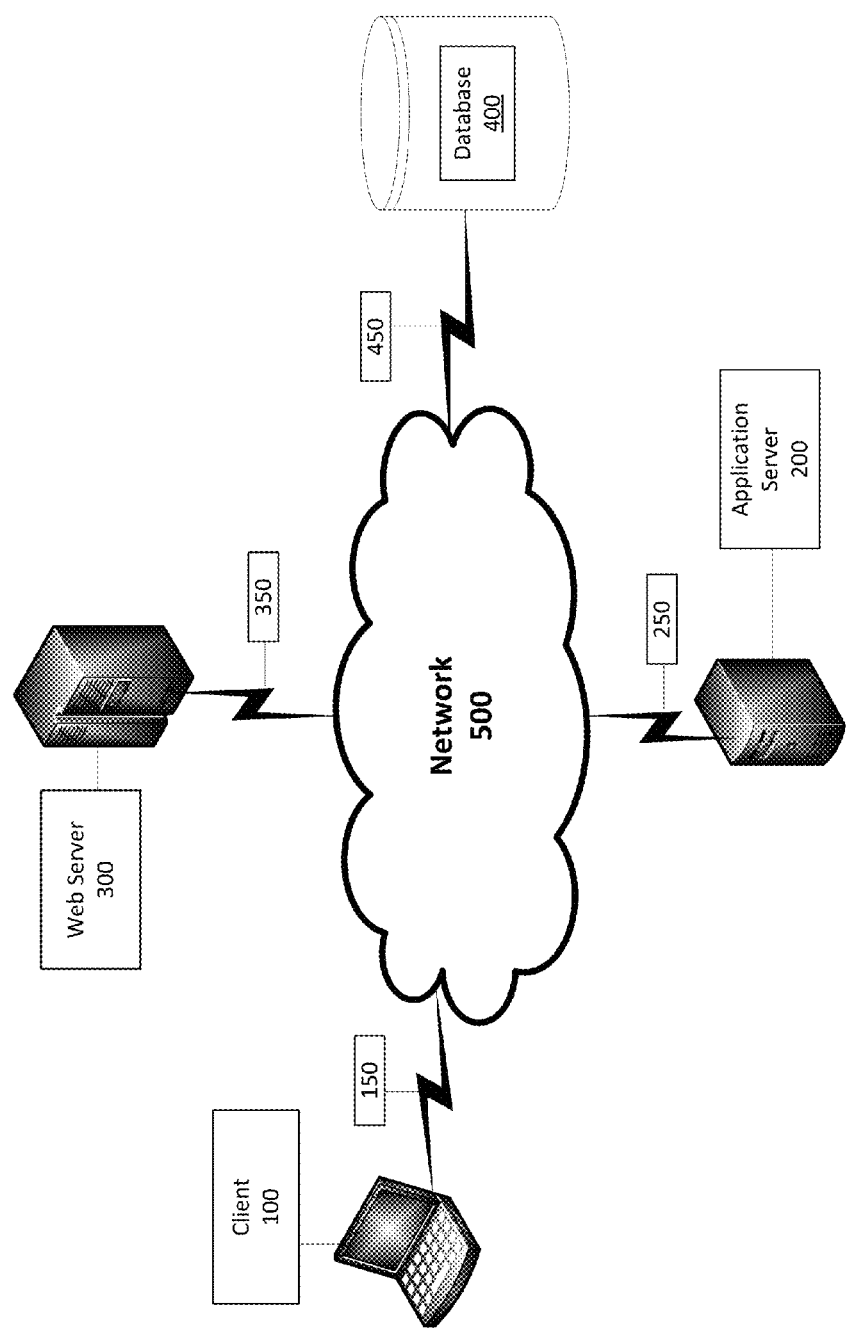
FIG. 1 is a diagram illustrating an exemplary environment for implementation of one embodiment.

Embodiments of the invention provide systems and methods for predictive clinical planning, design, and integrated execution services.

Prior to the mass production and sale of a particular pharmaceutical product for the treatment of a medical condition in a human patient, clinical trials are conducted to determine the safety and efficacy of those pharmaceuticals. The clinical trial process requires massive investments of capital, time, and risk. Clinical trials often last periods of months, and frequently years, before a particular pharmaceutical product receives regulatory approval and is deemed effective and safe for the use of the general public.

The clinical trial process is typically carried out by multiple teams of investigators and researchers spread over a significant geographic area. This is often necessary because of the number of volunteer subjects required to obtain useful data on the safety and efficacy of the pharmaceutical product. Large populations are needed to obtain valid data because data tends to be more statistically reliable when sample sizes are larger; volunteers of varying demographics ensure that the pharmaceutical product works consistently and predictably across different demographics; it is challenging to secure the commitment of reliable volunteer subjects; and regulations require that the pharmaceutical be tested over a wide number of volunteer subjects to minimize any doubts regarding safety and efficacy.

Consequently, clinical trials are logistically and administratively demanding. It is difficult to coordinate and exchange information between teams of investigators. The information systems used by clinical trial teams vary, and the transfer of data from one stage of a clinical trial to the next is error-prone, costly, and repetitive. Furthermore, it is challenging to alter the specifications of the clinical trial plan and subsequently predict how those changes will impact the cost, accuracy, and logistical difficulty of the trial.

Embodiments of the invention provide systems and methods for clinical program management. In some embodiments, the method comprises one or more users developing a strategic map of a proposed clinical plan. The clinical plan may comprise one or more of: a draft launch label attribute, one or more strategies, and a schema. In some embodiments, the method also comprises linking the clinical plan and schema to one or more trials. The method may also comprise subsequently linking the trials to one or more objectives and measures. Further, the method may also comprise subsequently linking none, one, or a plurality of objectives to none, one, or a plurality of measures. In some embodiments, the method further comprises identifying patient criteria. The method may also comprise enrolling patients from one or more investigator sites. The investigator sites may be located in one or more countries. The method may also comprise integrating the clinical plan with a clinical plan execution application.

Some embodiments provide a schema designer. The schema designer may provide a means by which a user can perform one or more of the following: enter data related to a clinical trial, view a visualization of the events comprising that clinical trial, and make changes to the clinical trial. In some embodiments, the system graphically displays all of the information entered regarding the clinical trial. In other embodiments, a logically-grouped subset of information is provided. Further, as new data is entered into the system, the graphic representations may be automatically and dynamically updated such that any user in any location may access and view the updated graphic representations.

Some embodiments also provide a digital design canvas which facilitates the planning, design, and adjustment of a clinical trial. The canvas may allow a user to create, access, and alter protocol elements of a clinical trial without the need to manually re-enter information across disparate systems or formats. In some embodiments, the canvas integrates the schema and the schedule of events for a clinical trial such that changes to either are automatically reflected in the other.

Referring now to the drawings, in which like numerals indicate like elements throughout the several figures, FIG. 1 is a diagram illustrating an exemplary environment for implementation of one embodiment of the invention. The embodiment shown in FIG. 1 includes a client 100 that allows a user to interface with an application server 200, web server 300, and/or database 400 via a network 500.

The client 100 may be, for example, a personal computer (PC), such as a laptop or desktop computer, which includes a processor and a computer-readable media. The client 100 also includes user input devices, such as a keyboard and mouse or touch screen, and one or more output devices, such as a display. In some embodiments of the invention, the user of client 100 accesses an application or applications specific to one embodiment of the invention. In other embodiments, the user accesses a standard application, such as a web browser on client 100, to access applications running on a server such as application server 200, web server 300, or database 400. For example, in one embodiment, in the memory of client 100 are stored applications including a design studio application for planning and designing clinical trials. The client 100 may also be referred to as a terminal in some embodiments of the present invention.

Such applications may be resident in any suitable computer-readable medium and executable on any suitable processor. Such processors may comprise, for example, a microprocessor, an ASIC, a state machine, or other processor, and can be any of a number of computer processors, such as processors from Intel Corporation, Advanced Micro Devices Incorporated, and Motorola Corporation. The computer-readable media stores instructions that, when executed by the processor, cause the processor to perform the steps described herein.

The client 100 provides a software layer, which is the interface through which the user interacts with the system by receiving and displaying data to and from the user. In one embodiment, the software layer is implemented in the programming language C# (also referred to as C Sharp). In other embodiments, the software layer can be implemented in other languages such as Java or C++. The software layer may be graphical in nature, using visual representations of data to communicate said data to one or more users. The visual representations of data may also be used to receive additional data from one or more users. In one embodiment, the visual representation appears as a spider-like layout of nodes and connectors extending from each node to a central node.

Embodiments of computer-readable media comprise, but are not limited to, an electronic, optical, magnetic, or other storage device, transmission device, or other device that comprises some type of storage and that is capable of providing a processor with computer-readable instructions. Other examples of suitable media comprise, but are not limited to, a floppy disk, CD-ROM, DVD, magnetic disk, memory chip, ROM, RAM, PROM, EPROM, EEPROM, an ASIC, a configured processor, all optical media, all magnetic tape or other magnetic media, or any other medium from which a computer processor can read instructions. Also, various other forms of computer-readable media may be embedded in devices that may transmit or carry instructions to a computer, including a router, private or public network, or other transmission device or channel, both wired and wireless. The instructions may comprise code from any suitable computer-programming language, including, for example, C, C++, C#, Visual Basic, Java, Python, Perl, and JavaScript.

The application server 200 also comprises a processor and a memory. The application server may execute business logic or other shared processes. The application server may be, for example, a Microsoft Windows Server operating in a .NET framework, an IBM Weblogic server, or a Java Enterprise Edition (J2E) server. While the application server 200 is shown as a single server, the application server 200, and the other servers 300, 400 shown may be combined or may include multiple servers operating together to perform various processes. In such embodiments, techniques such as clustering or high availability clustering may be used. Benefits to architectures such as these include redundancy and performance, among others.

In the embodiment shown in FIG. 1, the application server 200 is in communication with a web server 300 via a network connection 250. The web server 300 also comprises a processor and a memory. In the memory are stored applications including web server software. Examples of web server software include Microsoft Internet Information Services (IIS), Apache Web Server, and Sun Java System Web Server from Oracle, among others.

In the embodiment shown in FIG. 1, the web server 300 is in communication with a database 400 via a network connection 350 and a network connection 450. The web server 300 provides a web service layer that, together or separate from application server 200, acts as middleware between a database 400 and the software layer, represented by the client 100. The web server 300 communicates with the database 400 to send and retrieve data to and from the database 400.

The network 500 may be any of a number of public or private networks, including, for example, the Internet, a local area network ("LAN"), or a wide area network ("WAN"). The network connections 150, 250, 350, and 450 may be wired or wireless networks and may use any known protocol or standard, including TCP/IP, UDP, multicast, 802.11b, 802.11g, 802.11n, or any other known protocol or standard. Further, the network 100 may represent a single network or different networks. As would be clear to one of skill in the art, the client 100, servers 200, 300, and database 400 may be in communication with each other over the network or directly with one another.

The database 400 may be one or a plurality of databases that store electronically encoded information comprising the data required to plan, design, and execute a clinical trial. In one embodiment, the data comprises one or more design elements corresponding to the various elements related to one or more clinical trials. The database 400 may be implemented as any known database, including an SQL database or an object database. Further, the database software may be any known database software, such as Microsoft SQL Server, Oracle Database, MySQL, Sybase, or others.

Figure 2:
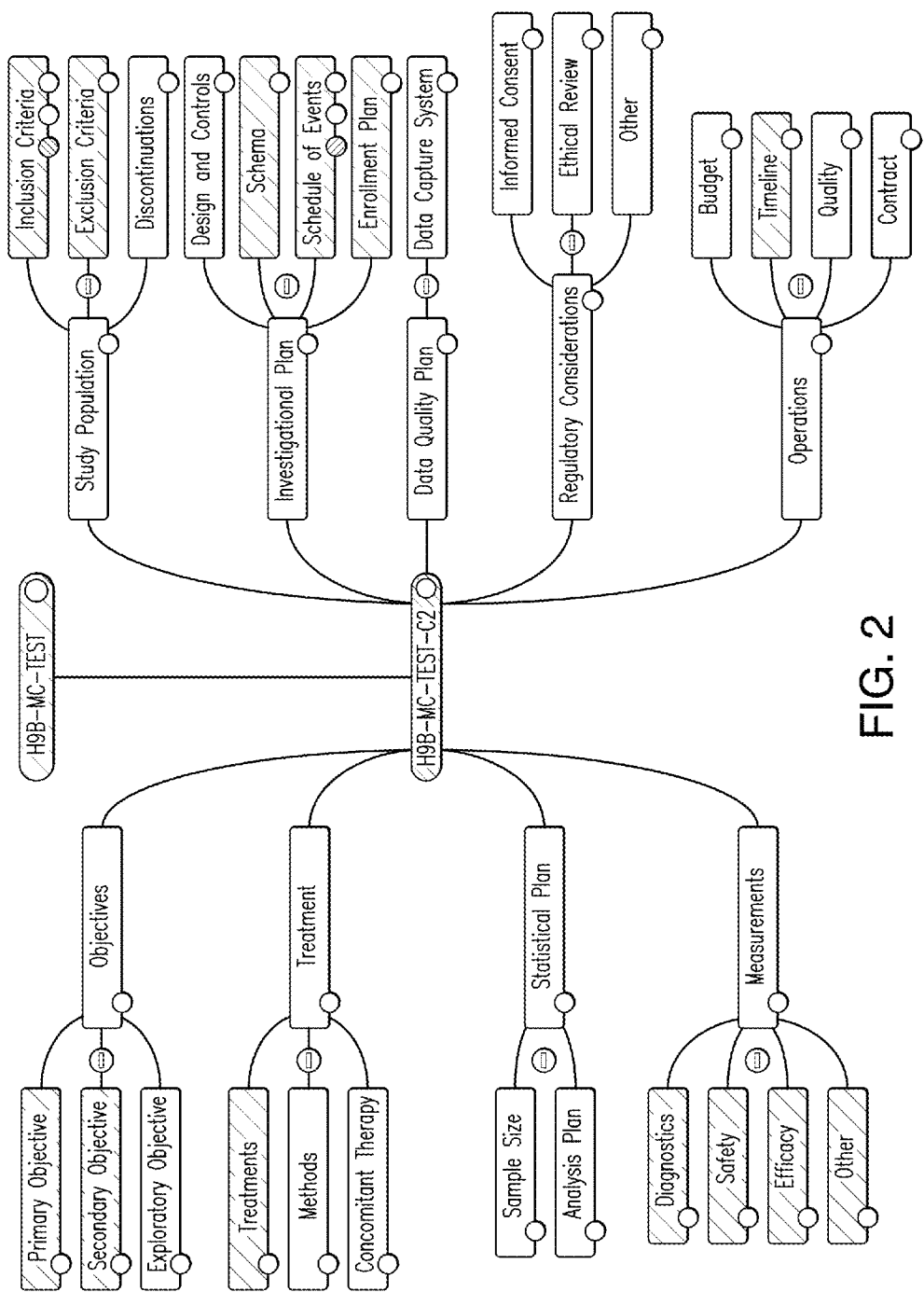
FIG. 2 is a diagram illustrating a context map according to one embodiment.

FIG. 2 is a diagram illustrating a context map according to one embodiment. A context map is a representation of the bounded contexts involved in a project and the actual relationships between them and their models. For example, the context map in FIG. 2 depicts the relationships of the objectives associated with a clinical trial.

FIG. 2 is described herein in reference to the illustrative environment shown in FIG. 1. However, the process is not limited to execution within that environment. In one embodiment, a context map, as shown in FIG. 2 is generated by the application server 200 and displayed on the client 100.

As shown in FIG. 2, the context map includes multiple nodes, each of which represents a design element. In one embodiment, the context map includes an objectives node, a treatment node, a statistical plan node, a measurements node, a study population node, an investigational plan node, a data quality plan node, a regulatory considerations node, and/or an operations node.

In the embodiment shown in FIG. 2, the context map includes one or more sub-nodes extending from each node. For example, the objectives node includes a primary objective sub-node, a secondary objective sub-node, and an exploratory objective sub-node. A user who is viewing and interacting with the context map via the client 100 may then use the sub-nodes to enter information regarding the primary objective(s), secondary objective(s), and/or any exploratory objective(s). Correspondingly, the user may enter information regarding other sub-nodes as well.

In various embodiments, using a context map, such as the one disclosed in FIG. 2, provides significant flexibility to the individual(s) designing a clinical trial. For example, during the early stage of trial design, the information entered may be very high level. At such a stage, the designer(s) may have a rough idea of the inclusion and exclusion criteria for the study population and may thus enter the information in the inclusion criteria and/or exclusion criteria sub-nodes of the study population node.

In one embodiment, when a user selects a particular node or sub-node, graphic representations appear primarily as either dashboards or editors that are configured to receive and present data to one or more users. In various embodiments, dashboards provide representations of various sets of data within the system. Selecting a node in a dashboard will launch a corresponding editor. Editors comprise interfaces through which one or more users inputs design parameters which are combined with proprietary and outsourced data and then displayed as graphs to show the impact of user choices.

In one embodiment, a graphic representation may consist of menus and text entry fields from which one or more users may instantiate a clinical trial by selecting an existing molecule or entering a new molecule candidate. In some embodiments, an existing molecule or a new molecule candidate is a chemical compound used for pharmaceutical treatment, or a proposed chemical compound intended to be used for pharmaceutical treatment. Additional information may be entered from this graphic representation, for example candidate details such as a display name, full title, candidate names, disease indication or indications, and phase of development.

In one embodiment, a graphic representation may consist of images, symbols, and text arranged in panels and panes to provide one or more users the ability to search through information pertaining to clinical trials stored within the system. Panels and panes may consist of, for example, catalogs, search panels, and design canvases. A catalog comprises an interface where shortcuts to access molecules, clinical plans, and trial candidates may be selected to launch corresponding dashboards and editors or to display schemas of selected trial candidates in the design canvas. A search panel comprises an interface that may be used to reduce the number of trial candidates displayed in the design canvas according to selected trial facets. A design canvas comprises the representation of information such as dashboards and editors or to display schemas of selected trial candidates requested by the user or a plurality of users. In some embodiments, a design canvas may comprise the output of a faceted search.

Figure 3:
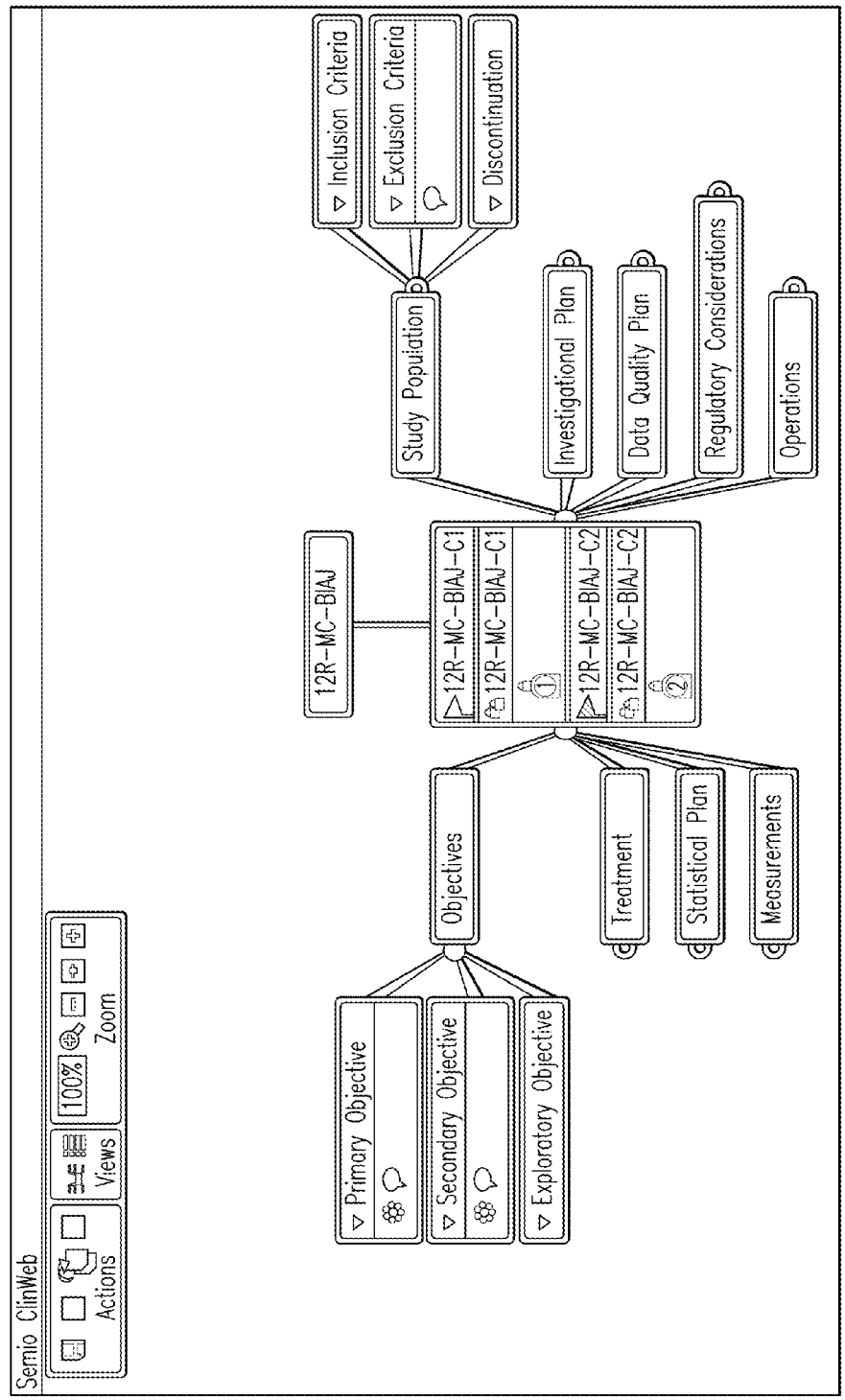
FIG. 3 is a diagram illustrating a trial comparator according to one embodiment.

FIG. 3 is a diagram illustrating a trial comparator according to one embodiment. There can be a benefit to comparing multiple trial candidates and identifying which elements of the candidates differ. This allows a user to quickly identify the differences and can help in determining which trial to pursue or whether to make changes to a candidate. In some embodiments, a graphic representation comprising a trial comparator that graphically overlaps selected trial candidates is provided. In some embodiments, the trial comparator and visually indicates, with a haloing or highlighting effect, which elements of the selected trials differ. This is shown in FIG. 3, where the primary objective, secondary objective, and exploratory objectives are hallowed, as well as the exclusion criteria. In some embodiments, the trial comparator is accessed by selecting trial candidates from a catalog and selecting a trial comparator button.

Figure 4:
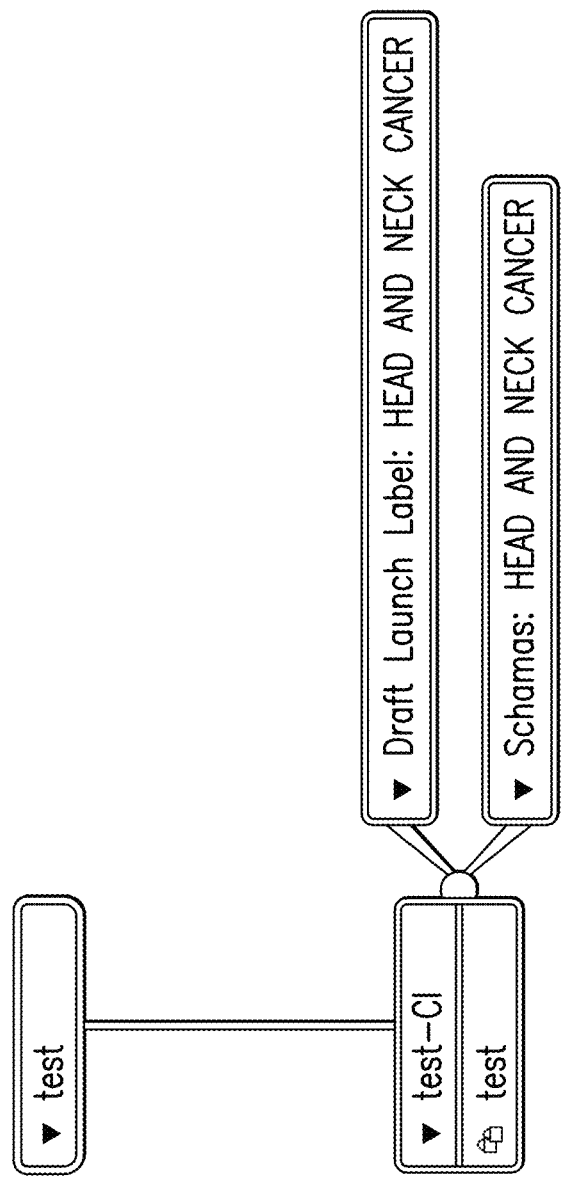
FIG. 4 is a diagram illustrating a clinical plan dashboard according to one embodiment.

FIG. 4 is a diagram illustrating a clinical plan dashboard according to one embodiment. In order to create a clinical plan schema, some embodiments provide a clinical plan dashboard which allows a user to select a schema in order to open for viewing or editing. In the embodiment illustrated in FIG. 4, a clinical plan dashboard comprises nodes configured to launch dashboards and editors for creating clinical plan schemas and strategies. In some embodiments, nodes in a clinical plan dashboard for which data has not been entered are highlighted in some manner. An example is shown in FIG. 4, where the DLL and schemas nodes are gray which indicates that the data corresponding to the DLL and schemas has not yet been entered.

Figure 5:
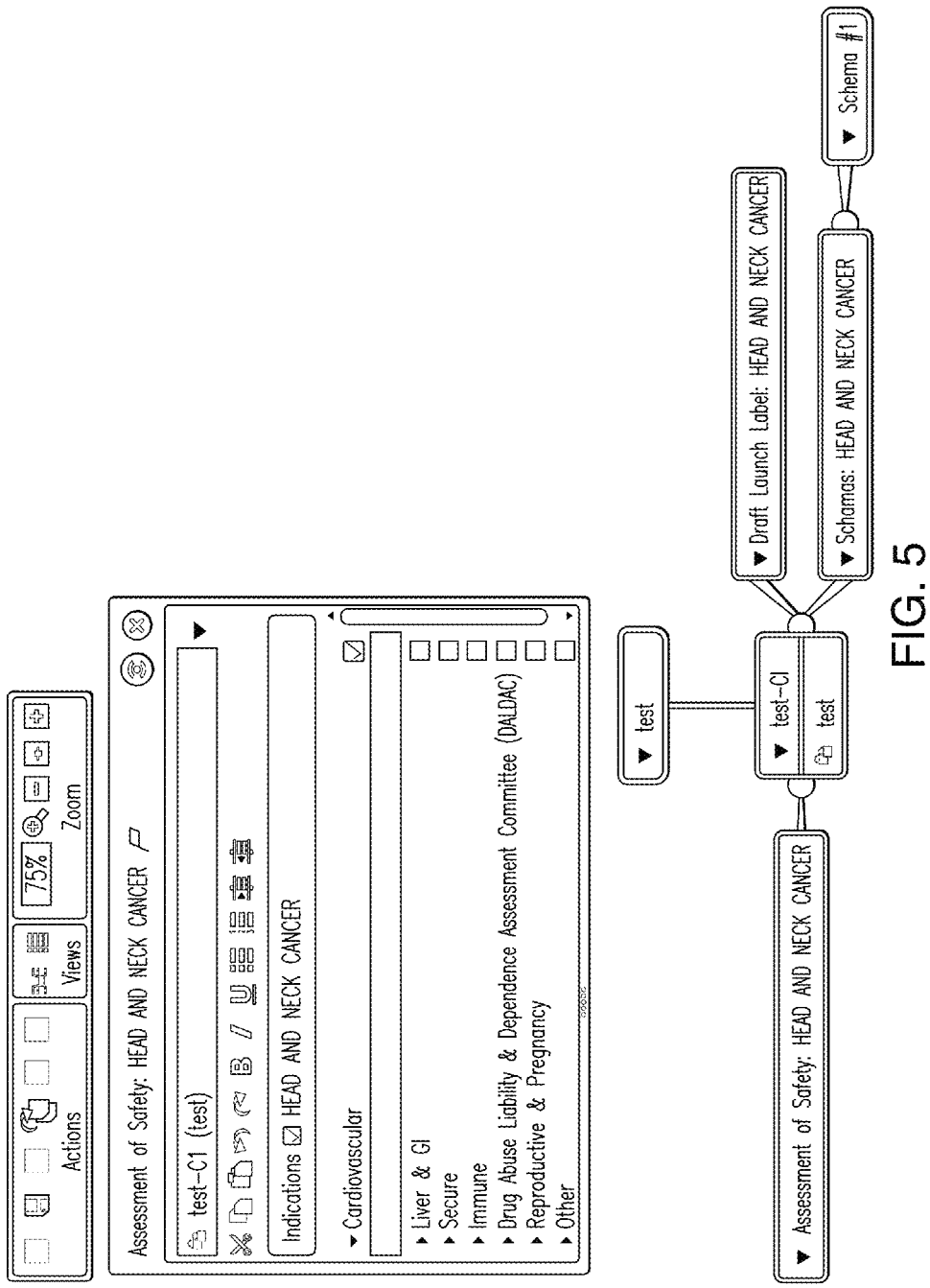
FIG. 5 is a diagram illustrating a strategy editor according to one embodiment.

FIG. 5 is a diagram illustrating a strategy editor according to one embodiment. In some embodiments, a strategy editor comprises an already created schema and associated information, and is configured to allow one or more users to enter additional data relating to a specific strategy. The embodiment depicted in FIG. 5 illustrates a strategy editor that is configured to enter data corresponding to the assessment of safety strategy for a particular schema. A specific strategy editor may be instantiated by selecting a particular node from a clinical plan dashboard.

Figure 6:
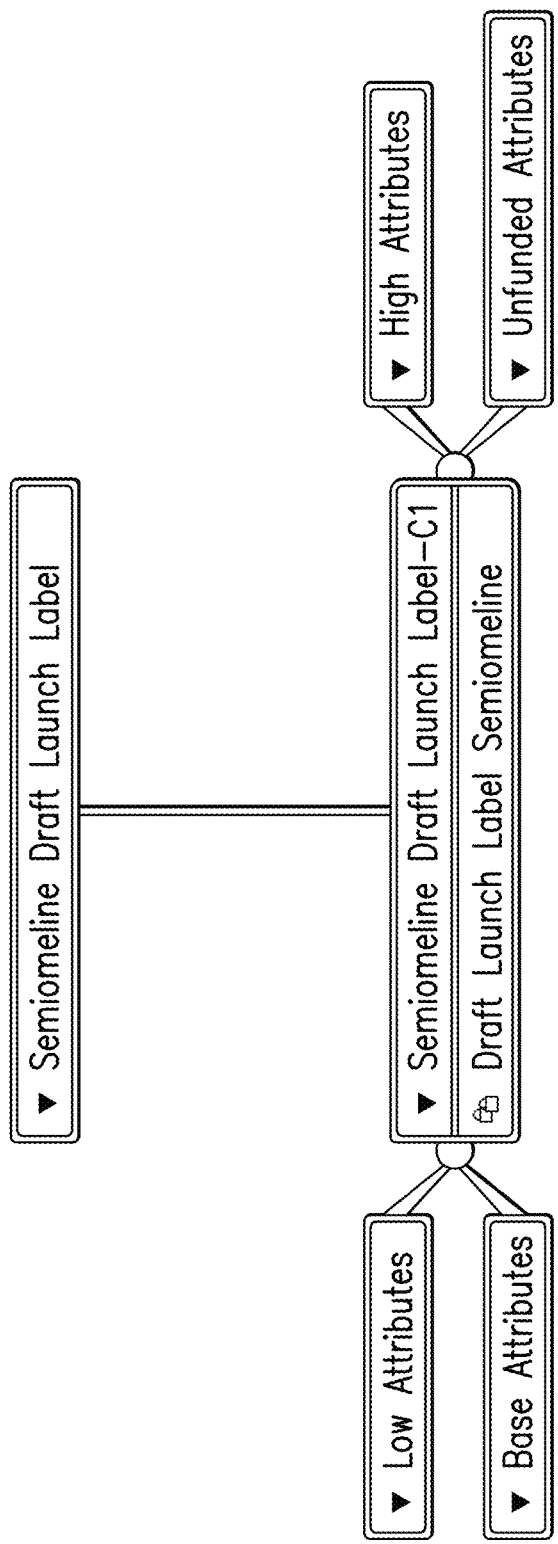
FIG. 6 is a diagram illustrating a draft launch label (DLL) dashboard according to one embodiment.

FIG. 6 is a diagram illustrating a draft launch label (DLL) dashboard according to one embodiment. In various embodiments, a DLL comprises multiple informational attributes, including low, high, base, and unfunded attributes. Low attributes comprise requirements of a particular clinical plan, base attributes comprise the most likely outcomes of a clinical plan, and high attributes comprise the most favorable outcomes of a clinical plan. In some embodiments, each attribute type is represented graphically by a node on the DLL dashboard. One or more users may select a node from a DLL dashboard to launch a corresponding editor to enter data for a particular attribute.

In one embodiment, as illustrated in FIG. 6, a DLL dashboard includes a main node (in one embodiment titled Semiomeline Draft Launch Label), a candidate node below the main node (in one embodiment titled Semiomeline Draft Launch Label-C1), and four attribute type nodes linked to the main node (in one embodiment titled Low Attributes, Base Attributes, High Attributes, and Unfunded Attributes).

Figure 7:
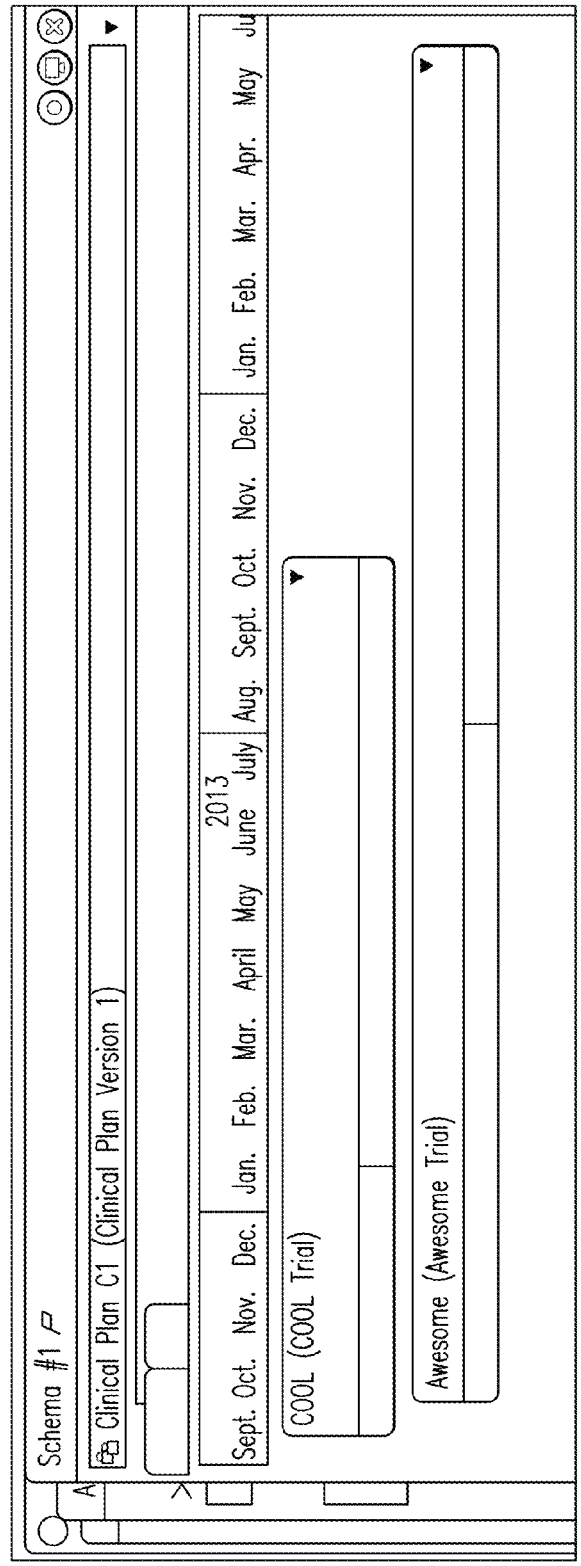
FIG. 7 is a diagram illustrating a clinical plan (CP) schema according to one embodiment.

FIG. 7 is a diagram illustrating a clinical plan (CP) schema according to one embodiment. In some embodiments, a CP schema comprises a visual timeline representation of the trials and milestones associated with a CP candidate. A CP schema may comprise one or more trials. For example, in the embodiment illustrated in FIG. 7, there are two trials: one named "COOL" and another named "Awesome." In such an embodiment, a trial dashboard may be instantiated by selecting it within a relevant CP schema. Thus, if a user selected "COOL," then the "COOL" trial dashboard would be launched. Correspondingly, if a user selected "Awesome," then the "Awesome" trial dashboard would be launched. Trials may be added to a CP schema by a user by selecting a button within the user interface.

Figure 8:
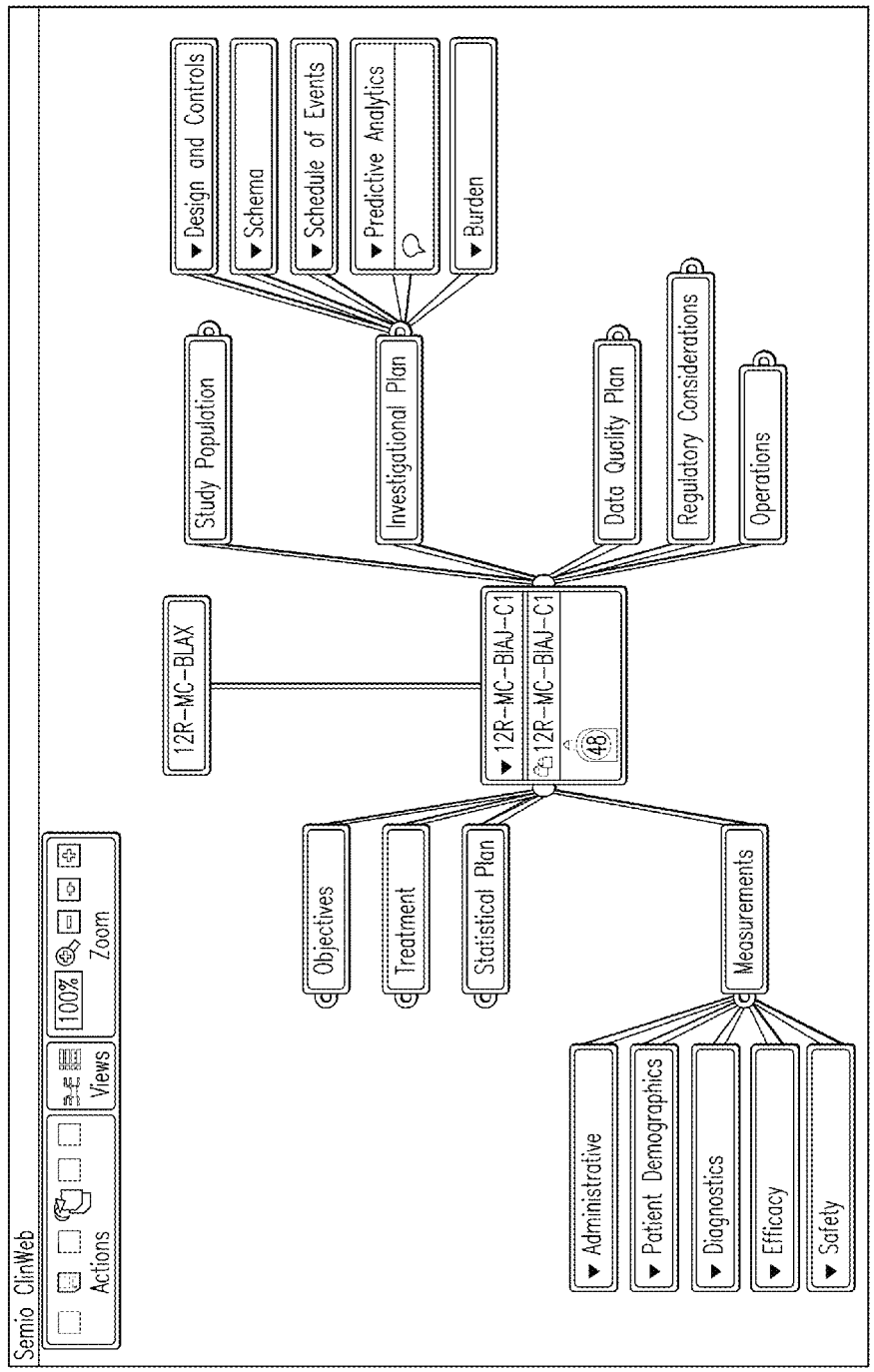
FIG. 8 is a diagram illustrating a trial dashboard according to one embodiment.

FIG. 8 is a diagram illustrating a trial dashboard according to one embodiment. In some embodiments, a trial dashboard comprises one or more nodes. The one or more nodes may correspond to editors and a predictive analytics dashboard, a main node, a candidate node, a plurality of nodes linked to the candidate node, and/or information depicting the predicted cost and patient burden of the trial candidate. In the embodiment illustrated in FIG. 8, a patient burden of 48 is shown below the candidate node. A patient burden is a value that represents the amount of burden that a particular test will place on a patient. For example, events such as a blood draw or a biopsy would yield a higher burden score, while merely filling out a short survey would yield a lower burden score.

In some embodiments, one or more nodes correspond to editors. When such a node is selected, this causes an editor to launch. An editor may allow a user to enter data. Examples of such data may include one or more of: objectives, treatments, diagnosis measures, efficacy measures, patient selection, enrollment, patient visit schedules, and trial candidate schemas.

In some embodiments, a graphic representation comprises an objectives editor. An objectives editor comprises a means by which a user may define trial candidate objectives. In some embodiments, each objective comprises text and association fields configured to indicate that the objective is associated with a measure.

In some embodiments, a graphic representation comprises a diagnostics editor. A diagnostics editor comprises a means by which one or more users may define and select diagnosis measures. A diagnostics editor may be instantiated from the schedule of events.

Figure 9:
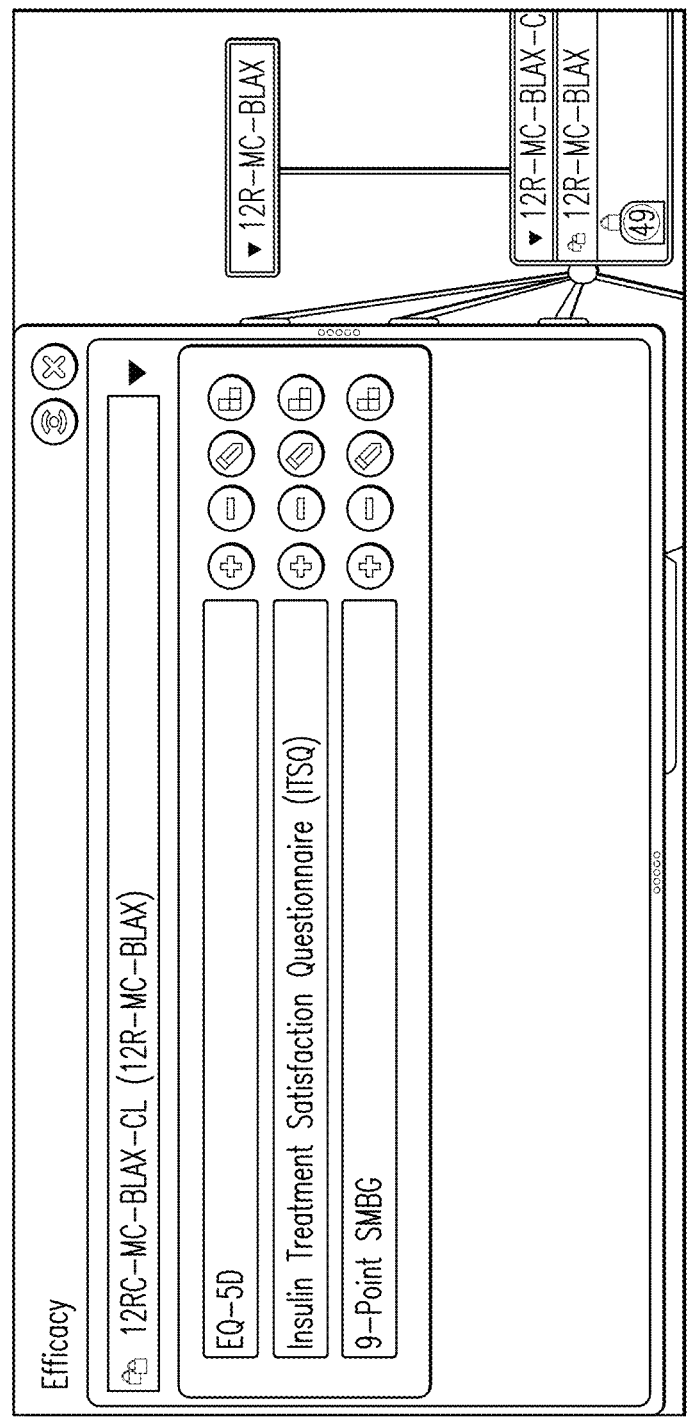
FIG. 9 is a diagram illustrating an efficacy editor according to one embodiment.

FIG. 9 is a diagram illustrating an efficacy editor according to one embodiment. In some embodiments, an efficacy editor comprises a means by which one or more users may define efficacy measures and associations. In the embodiment illustrated in FIG. 9, an efficacy editor includes a table of measures (including in one illustrative embodiment: EQ-5D, Insulin Treatment Satisfaction Questionnaire, and 9-point SMBG) and buttons configured to attach case report forms (CRFs) and associate objectives.

In some embodiments, after a CRF or objective is associated, the corresponding button changes color. Accordingly, by observing the table, a user can assess the overall status of the efficacy measures design.

Additionally, the efficacy editor may include an objective associator button. This button may be located beside the measure. In the embodiment illustrated in FIG. 9, an objective associator button is located to the right of each measure. For example, if a user clicked the objective associator button to the right of the EQ-5D measurement, the EQ-5D objective associator would be launched. When an efficacy measure is associated with an objective, this aggregates efficiency measurement resources invested to achieve the objective. However, in some instances no objective is associated with an efficiency measure. In such a case, it may be determined that such a measure is not necessary.

FIG. 10 is a diagram illustrating an objectives associator according to one embodiment. In some embodiments, an objectives associator comprises a means by which one or more users may associate objectives with efficacy measures. As discussed in the context of the embodiment illustrated in FIG. 9, if a user clicks the objectives associator button associated with a measurement in the efficacy editor, then the objectives associator is launched. In the embodiment illustrated in FIG. 10, a user has clicked the objective associator next to EQ-5D and as a result the objectives associator for EQ-5D was launched. In some embodiments, the objectives associator comprises a list of objectives and corresponding association buttons. In the embodiment illustrated in FIG. 10, the objectives associator includes a primary objective and a list of ten secondary objectives. In some embodiments, selecting an association button associates the corresponding objective with the efficacy measure from which the associator was instantiated.

Also, in some embodiments the objectives associator provides an indication when an efficacy measure and its corresponding objective have been associated. For example, in one embodiment the objectives associator button shows a checkmark and the objective selection button in the efficacy editor is colored blue to visually indicate an association.

In some embodiments, a graphic representation may comprise a study population editor. A study population editor comprises a means by which one or more users may input population inclusion and exclusion data. In some embodiments, a study population editor comprises drop-down menus and text fields for inputting data.

In some embodiments, a graphic representation may comprise a design and controls editor. A design and controls editor comprises a means by which one or more users may input data including one or more of: design, patient numbers, randomization, and extension data. In some embodiments, a design and controls editor comprises multiple pages or panes where patient numbers and design inputs may be inputted separately.

In some embodiments, a graphic representation may comprise an interventions editor. An interventions editor comprises a means by which one or more users may input data corresponding to the name, dosage, frequency, formulation, and administrative route of drugs administered to patients during each period and segment of a trial.

Figure 11:
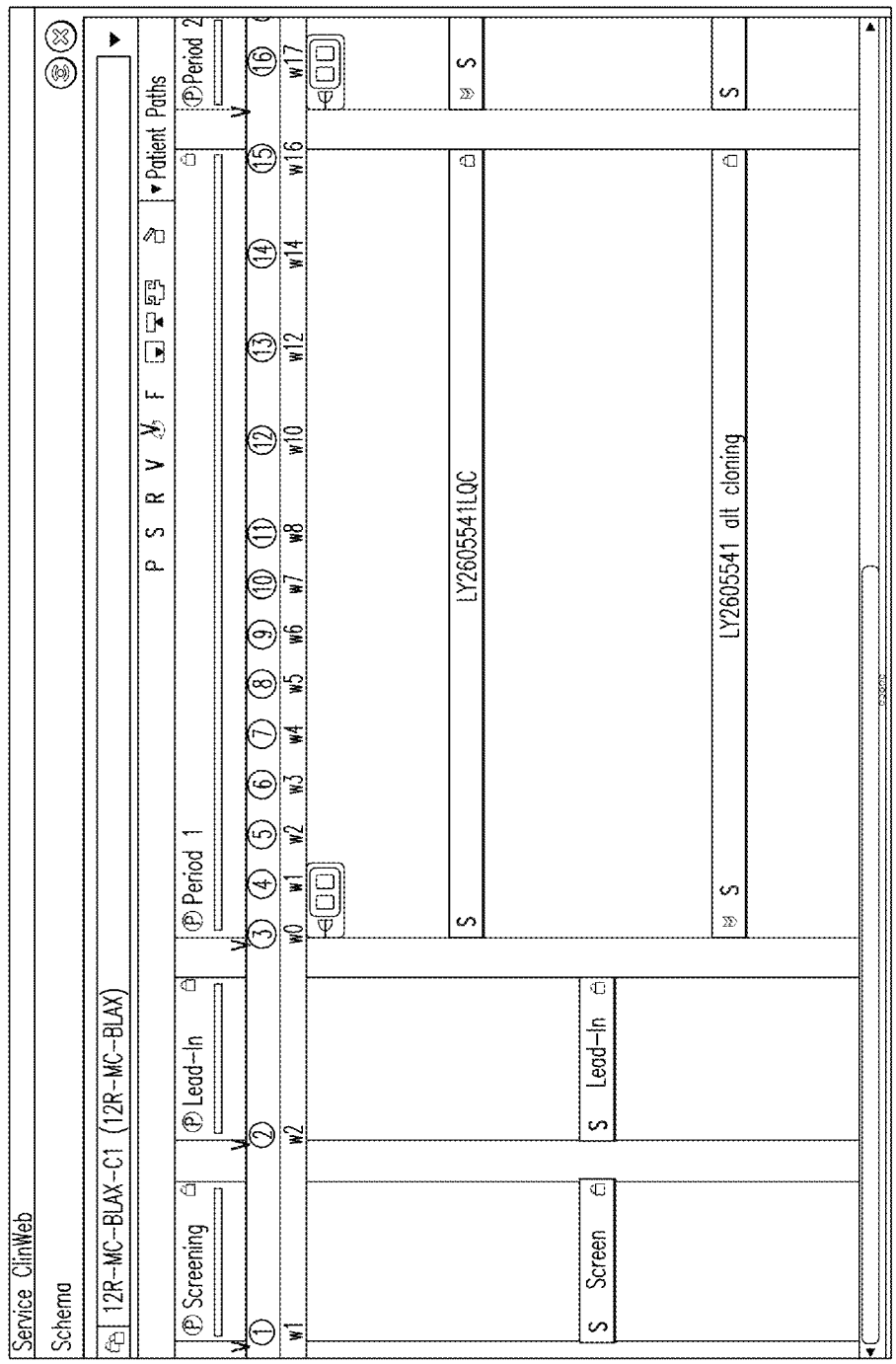
FIG. 11 is a diagram illustrating a schema editor according to one embodiment.

FIG. 11 is a diagram illustrating a schema editor according to one embodiment. In some embodiments, a schema editor comprises a means by which one or more users may add patient visits to a trial period and view data representing the structure of a trial candidate. For example, in the embodiment illustrated in FIG. 11, the schema editor shows a screening period, a lead-in period, two treatment arms for period one, and two treatment arms for period two. In a clinical trial, a treatment arm represents the treatment(s) to be provided to the patient(s) participating in the trial. In some embodiments, the schema editor allows a user to input information into the schedule of events and view patient data and measures created with the efficacy and diagnostic indicators.

Figure 12:
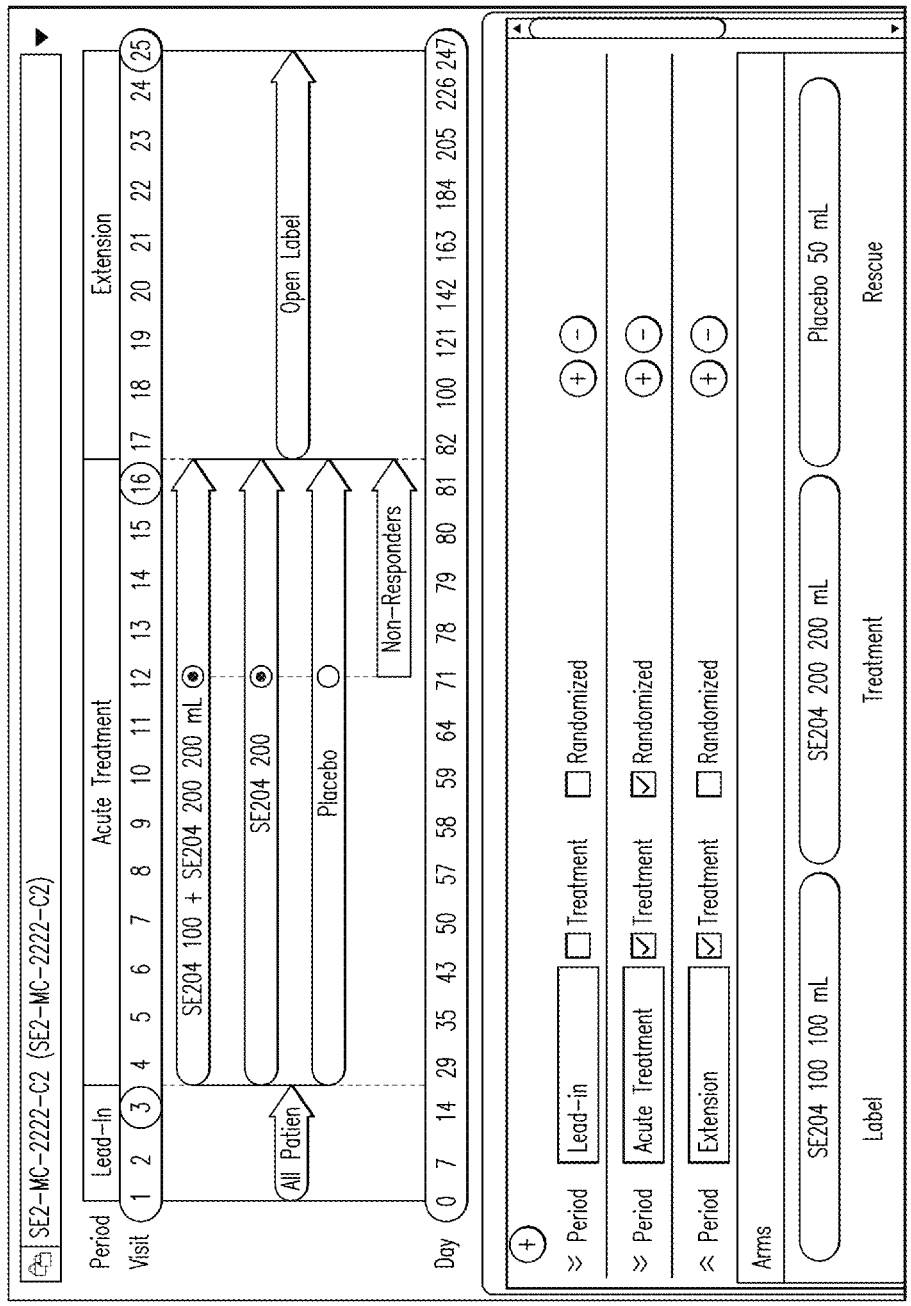
FIG. 12 is a diagram illustrating a schema editor according to another embodiment.

FIG. 12 is a diagram illustrating a schema editor according to another embodiment. In this embodiment, the schema editor illustrates the assignment of drugs to treatment arms. Here, a user may utilize the schema editor to enter information regarding drug assignments in a particular treatment arm.

In various embodiments, schema editors are provided in order to allow users to enter information regarding a variety of parameters.

Figure 13:
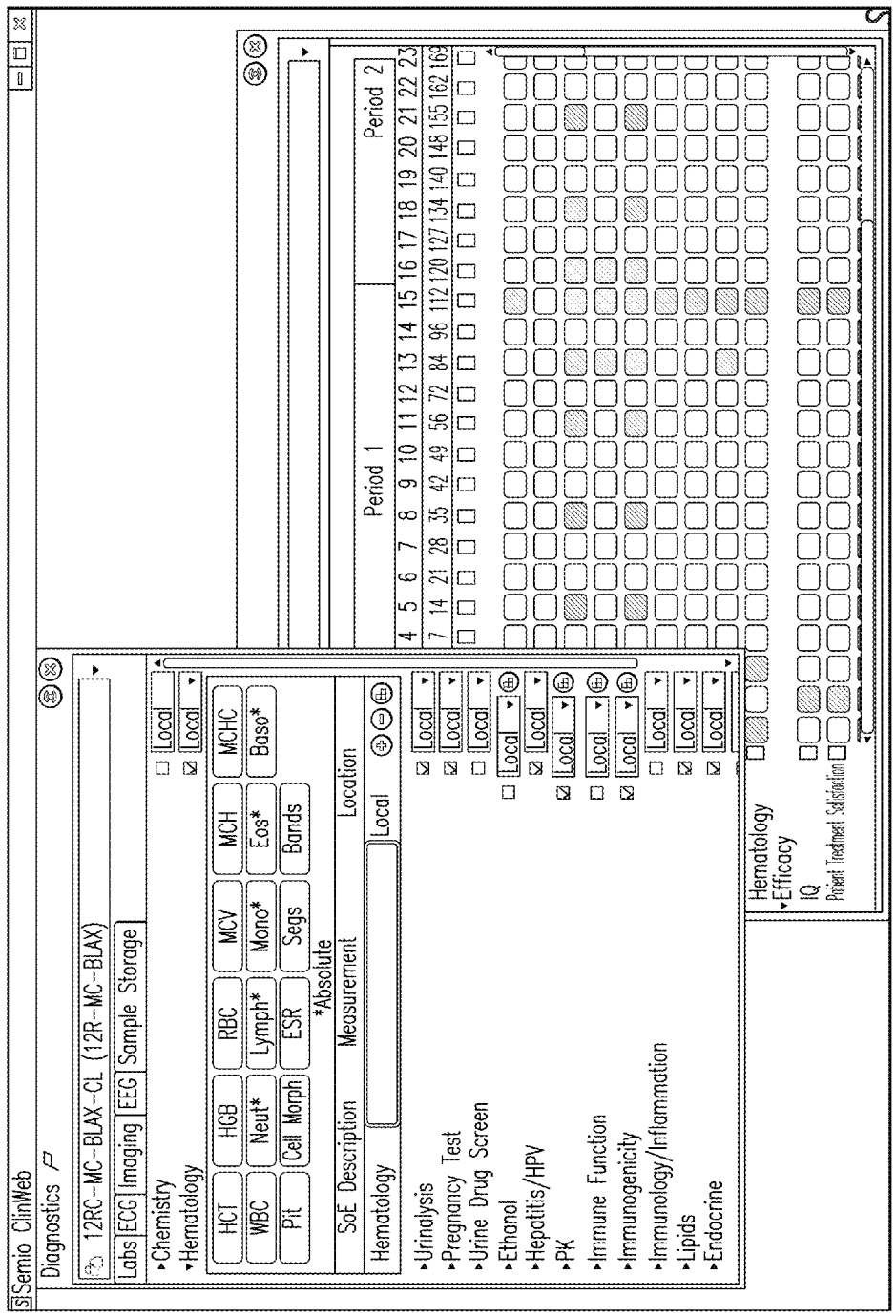
FIG. 13 is a diagram illustrating a schedule of events editor according to one embodiment.

FIG. 13 is a diagram illustrating a schedule of events editor according to one embodiment. In some embodiments, a schedule of events editor enables a user to designate what measures or corresponding samples will be obtained during which visits. In the embodiment illustrated in FIG. 13, a schedule of events editor view shows weeks on a horizontal axis and measures on a vertical axis. A diagnostics editor view may also be launched from a schedule of events editor in some embodiments.

Also, in some embodiments, the schedule of events editor pulls patient visit data from the schema. The schedule of events editor may also pull measures from a list of measures. The list may be created with an efficacy editor and/or a diagnostic editor, such as those described herein. In some embodiments, when a user selects the intersection of a row and column, the user selects a measure corresponding to the selected row to be obtained during a visit corresponding to the selected column. The selection may also drive cost and patient burden associated with the measures to the particular visit. Accordingly, costs and burden can be forecasted on a regular (e.g., weekly, bi-weekly, monthly) basis. Such a schedule may be delivered to those needing such information such as study teams.

In some embodiments, a burden editor is provided. A burden editor comprises a means by which one or more users may input patient burden data, such as the time required of a patient to obtain input for a measure, and then receive a patient burden score representing an abstraction of the relative burden on a patient corresponding to a particular clinical plan. A method is disclosed in which measures corresponding to various demands, requirements, and burdens imposed on a patient by a particular clinical plan are mathematically combined into a single numeric abstraction. Next, the numeric abstraction is displayed to a user. The numeric abstraction is sometimes referred to as a burden score. In some embodiments, this numeric abstraction (or burden score) provides a means by which one or more users may observe and predict the likelihood that a patient will participate in a clinical trial.

When a burden score is high, this indicates a burdensome trial which will likely make it more difficult to recruit patients to participate in the trial. In some embodiments, the overall burden of a particular trial candidate is displayed in the trial candidate dashboard.

Figure 14:
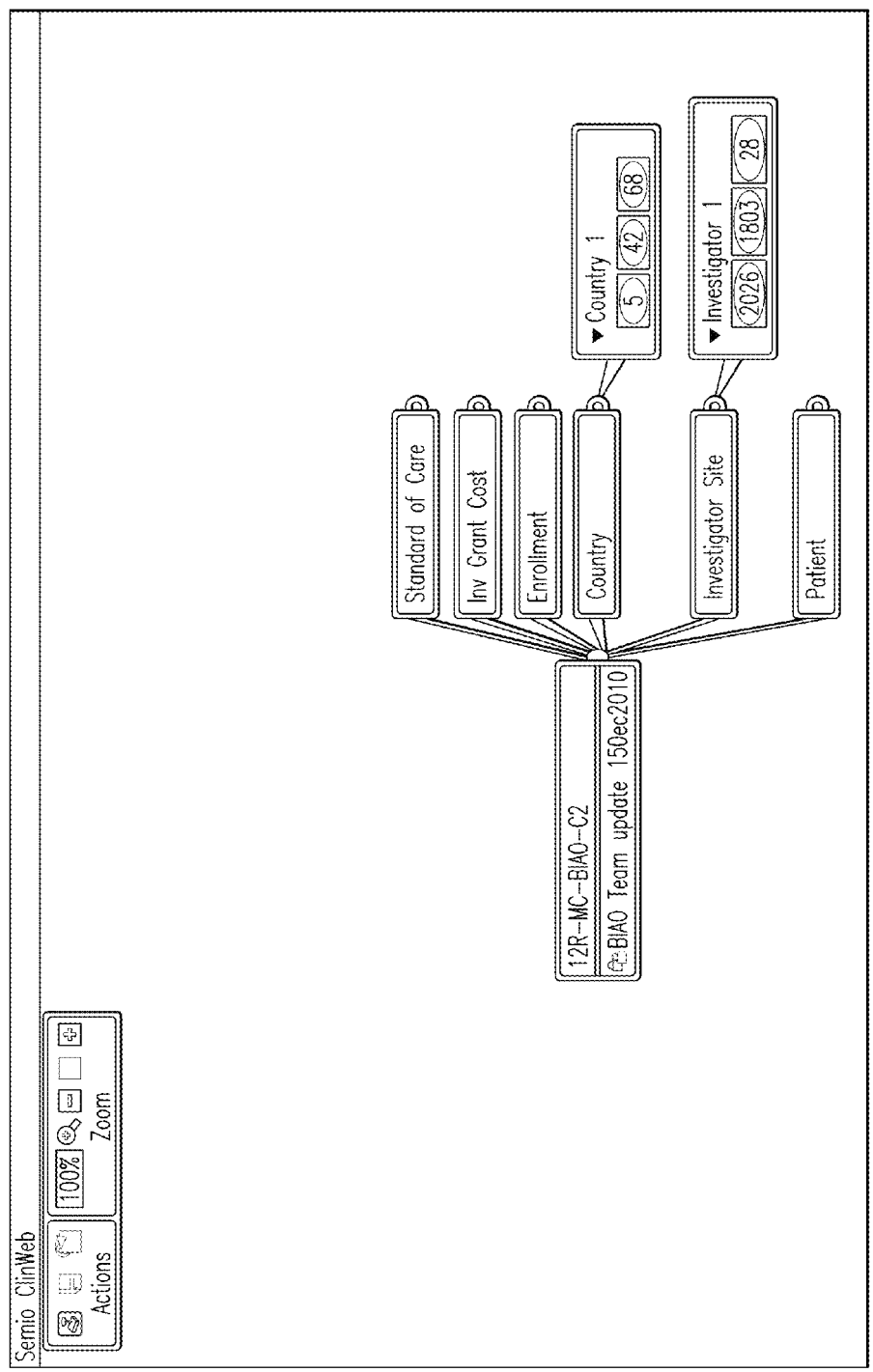
FIG. 14 is a diagram illustrating a predictive analytics dashboard according to one embodiment.

FIG. 14 is a diagram illustrating a predictive analytics dashboard according to one embodiment. In some embodiments, a predictive analytics dashboard comprises a means by which one or more users may instantiate one or more editors to enter and display enrollment or other data and combine said data with proprietary and/or outsourced data to predict the impact of user choices. In the embodiment illustrated in FIG. 14, the predictive analytics dashboard shows color-coded parameters of country and investigator site plans named "Country 1" and "Investigator 1." The color coding indicates the relative attractiveness of the particular courses of action. In some embodiments, the country and investigator site editors store country and investigator site plans that are subsequently accessed by the enrollment editor.

Figure 15:
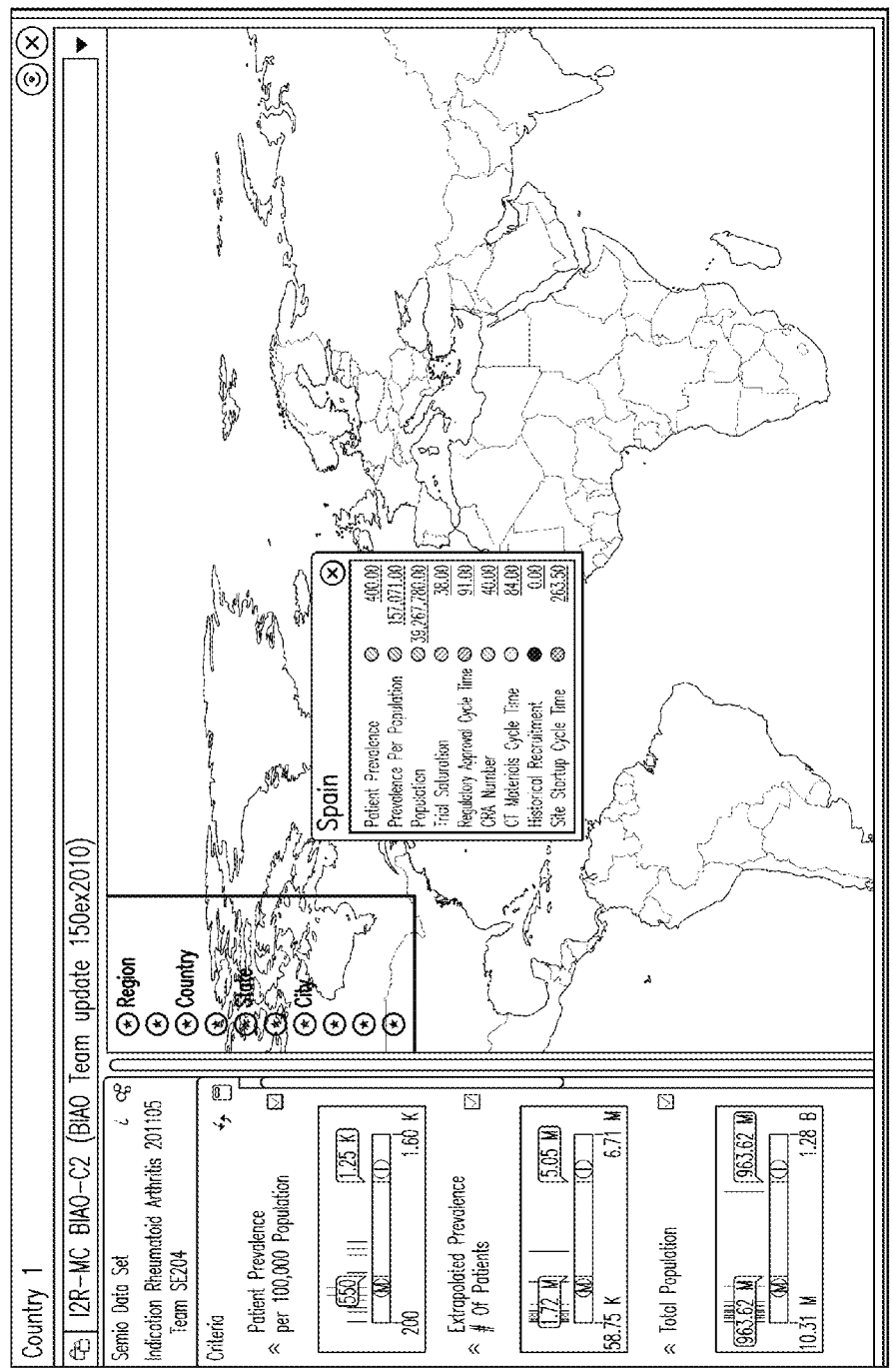
FIG. 15 is a diagram illustrating a country editor according to one embodiment.

FIG. 15 is a diagram illustrating a country editor according to one embodiment. In some embodiments, a country editor comprises a means by which one or more users may identify which countries have investigator sites likely to enroll the necessary patients for a clinical trial in a timely manner. This identification may be made based on proprietary historical information. In the embodiment illustrated in FIG. 15, a country editor may comprise sliders for setting limits for data categories. In such embodiments, the sliders divide the data range into three sub-ranges. Data falling within the first sub-range is assigned the number 0; data falling in the middle sub-range is assigned the number 1; and data in the last sub-range is assigned the number 2. Categories may be colored according to their assigned values. For example, 0, 1, and 2 may correspond to the colors red, yellow, and green, respectively.

In some embodiments, the values for all of the categories for a particular country are averaged to determine the value for the country. For example, the country may be colored red if the value falls below 0.8; the country may be colored yellow if the value is between 0.8 and 1.2; and the country may be colored green if the value exceeds 1.2. Also, a country may be colored a different color (e.g., gray or white) to indicate the country cannot be selected for one reason or another.

Further, data in one or more categories may be compared to user-designated limits in each category. Examples of such categories include patient prevalence, extrapolated prevalence, total population, trial saturation, regulatory approval cycle time, clinical trial materials cycle time, historical recruitment, and site startup cycle time. Next, based on the comparison between the data and the user-designated data limits, a value and associated color-code are created representing an abstraction of how attractive a particular country is for inclusion in the clinical plan.

Figure 16:
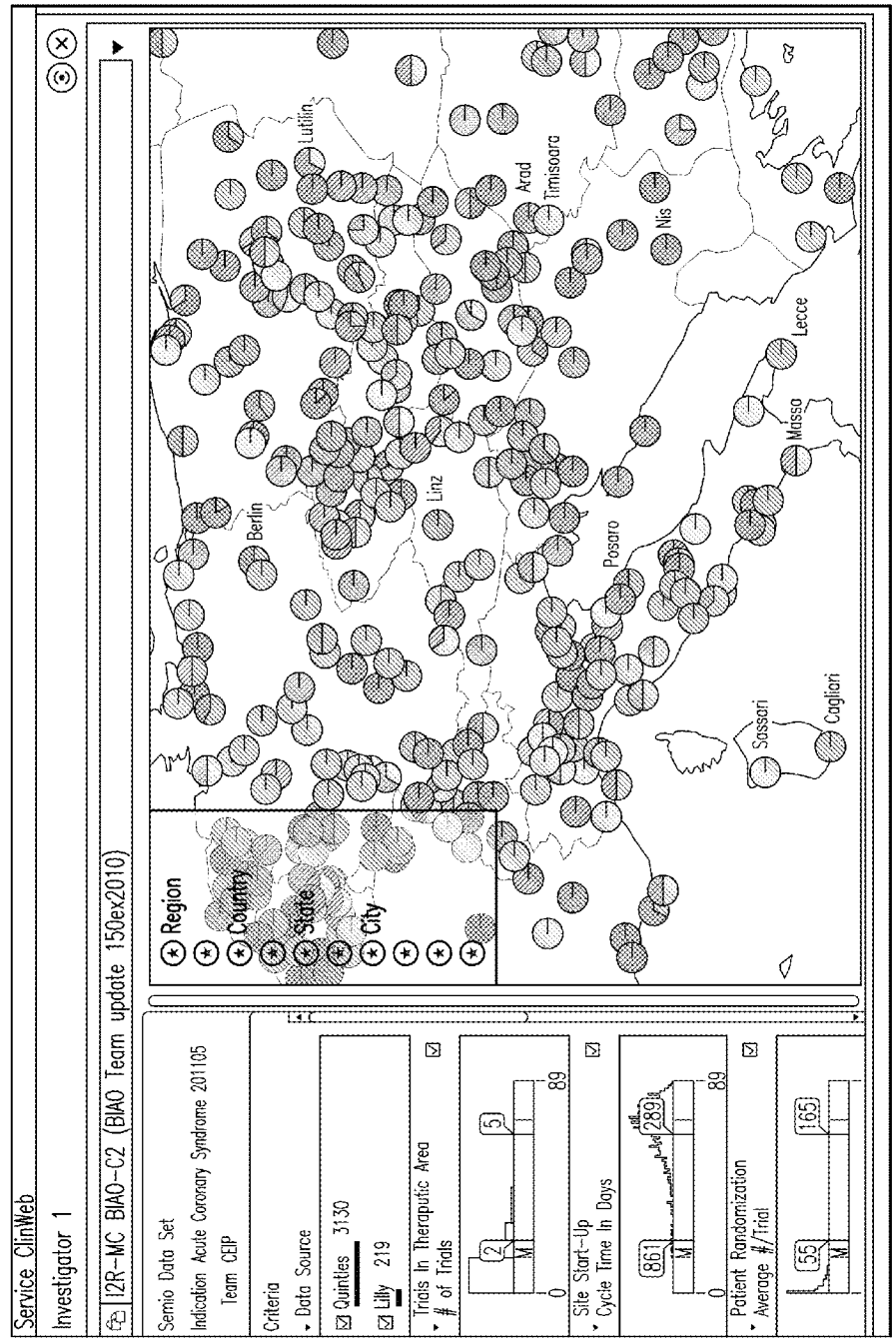
FIG. 16 is a diagram illustrating an investigator site editor according to one embodiment.

FIG. 16 is a diagram illustrating an investigator site editor according to one embodiment. In some embodiments, an investigator site editor comprises a means by which one or more users may view data representing the likelihood and timing of enrolling patients within geographical boundaries. In some embodiments, users can select geographical groupings such as countries, state, or cities for display. In some embodiments, data is represented to the user as color-coded circles representing the attractiveness of a particular investigator site. For example, the circles may be coded red, yellow, green, or some combination thereof.

FIGS. 17-22 are diagrams illustrating an enrollment editor according to various embodiments. In some embodiments, an enrollment editor allows a user to select an investigator site based on one or more criteria—for example, selected country and investigator site plans. According to one embodiment, an enrollment editor comprises one or more panels and panes that comprise tables, graphs, lists, and other representations of data. For example, in the embodiment illustrated in FIG. 17, an empty startup page is shown, signifying that no investigator site has been selected yet. A user may select one or more sites from the selection table by checking a selection button next to the desired site. As sites are added, the editor tallies various parameters, such as one or more of: the number of enrolled patients likely to be enrolled by the selected sites and/or site startup timing. For example, in the embodiment illustrated in FIG. 18, a results panel is shown which includes a country summary showing sites that have been selected as well as the tallied parameters. In this example, 1113 patients are required and the results panel shows that 318 sites were selected in order to enroll 1114 patients.

In some embodiments, a user can select between various enrollment models. One such model is competitive enrollment in which sites are added according to the user's selections until the required number of patients is reached. Another model is allocated enrollment in which site selection is restricted by patient rules, which can be created by the enrollment editor. An example of a patient rule is a requirement that at least 50 patients must be in Germany and no more than 50 patients may be in Saudi Arabia. Another exemplary rule requires enrollment only of investigators capable of providing at least 100 patients.

Figure 19:
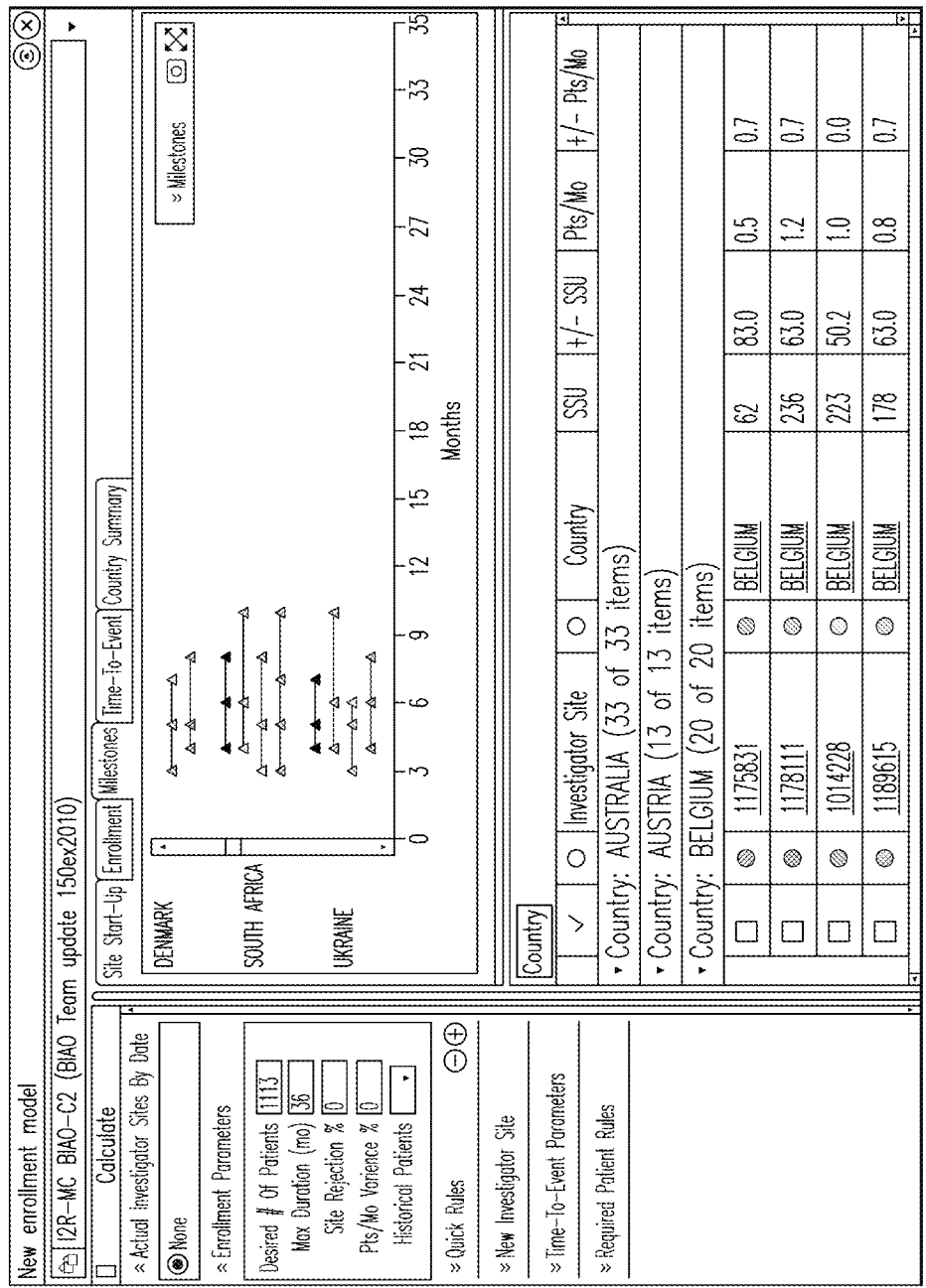
FIG. 19 is a diagram illustrating an enrollment editor according to one embodiment.

In the embodiment illustrated in FIG. 19, a graph is provided showing, in the results panel, the best, midline, and worst case first-patient visit milestones. In this embodiment, the middle milestone represents the median of the sites in the country and the best/worst cases are computed by the median $+/-\sigma$.

Figure 20:
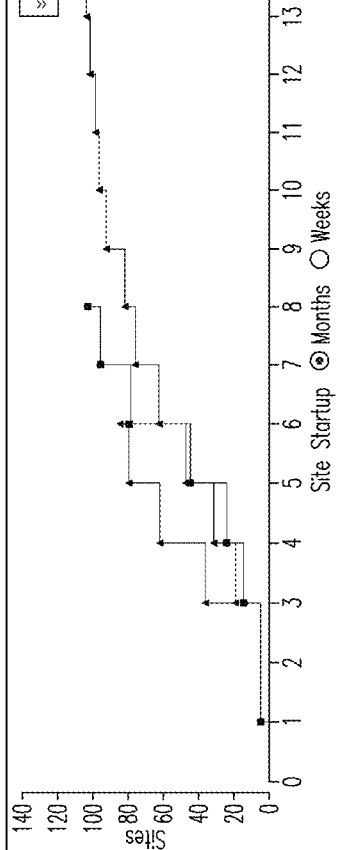
FIG. 20 is a diagram illustrating an enrollment editor according to one embodiment.
Figure 21:
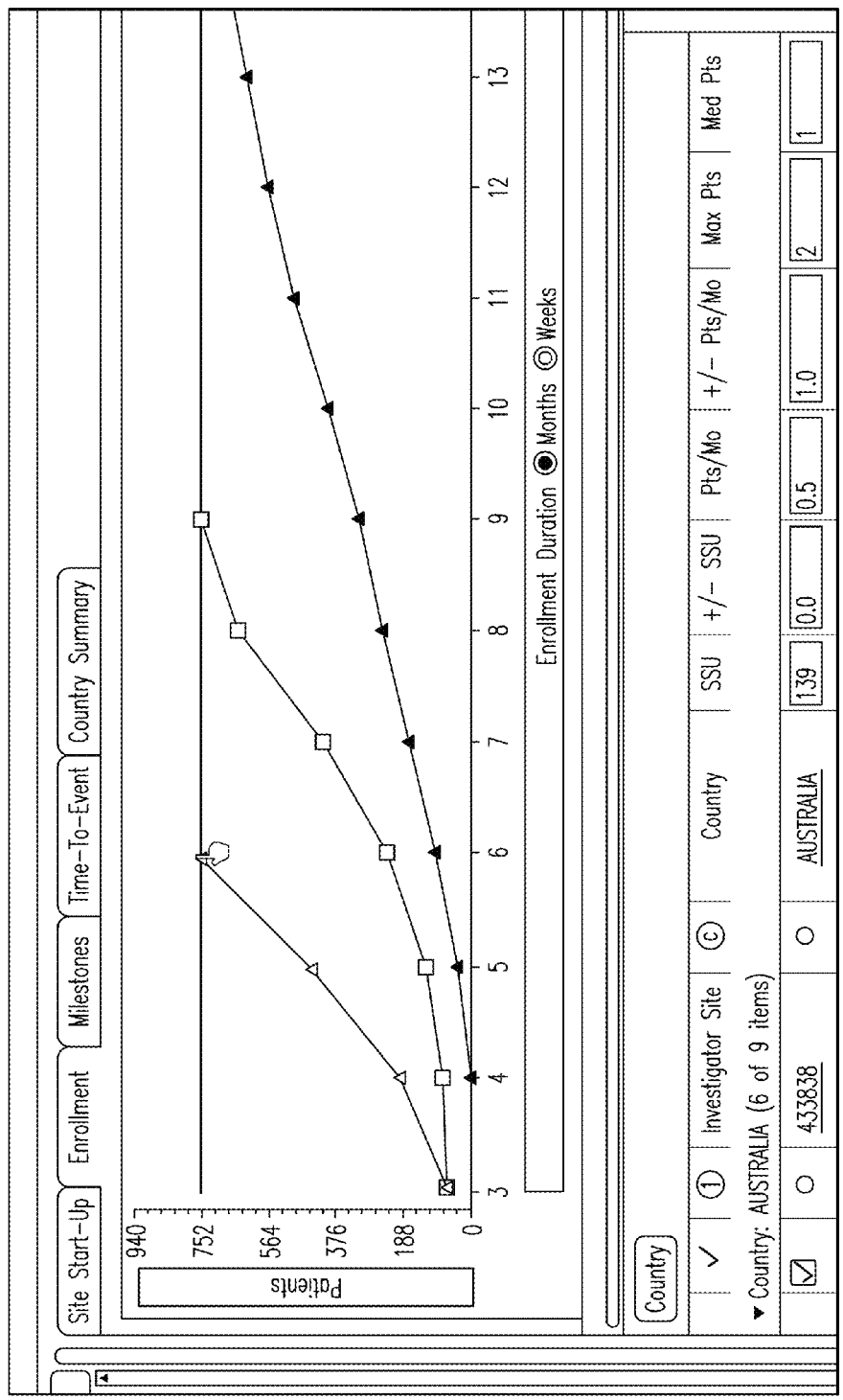
FIG. 21 is a diagram illustrating an enrollment editor according to one embodiment.
Figure 22:
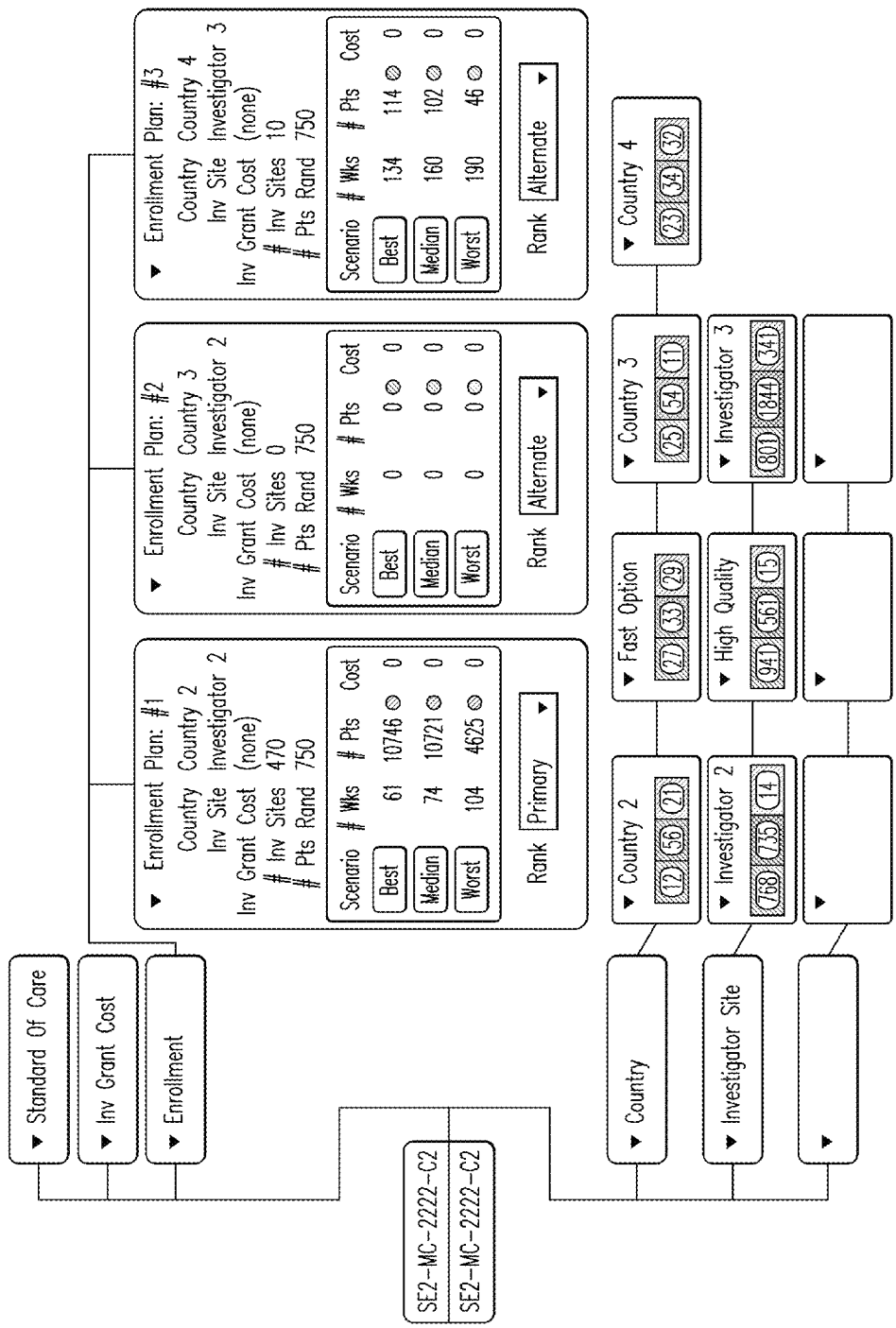
FIG. 22 is a diagram illustrating an enrollment editor according to one embodiment.

In various embodiments, other graphs are provided. For example, FIG. 20 illustrates a graph showing how quickly sites start up as the number of sites increases. Also, FIG. 21 illustrates a graph showing enrollment duration as the number of patients increases.

In some embodiments, the enrollment editor enables users to develop multiple enrollment plans based on different country and investigator site plans. In the embodiment illustrated in FIG. 22, enrollment plans are summarized on a predictive analytics dashboard. In the embodiment illustrated in FIG. 22, three enrollment plans, four country plans, and three investigator site plans are depicted. For each enrollment plan (labeled "Enrollment Plan #1," "Enrollment Plan #2," and "Enrollment Plan #3"), the best, median, and worst case is shown. Also, for each country and investigator plan, the number of red, yellow, and green countries and investigator sites are shown.

In some embodiments, each enrollment plan is designated as primary, secondary, or alternate. There can only be one primary enrollment plan. The primary plan can be published by selecting the appropriate menu option from the primary plan node. In some embodiments, upon selection of the publication option, the user must also select a publication label. Examples of publication labels include forecast, re-forecast, baseline, or re-baseline.

Figure 23:
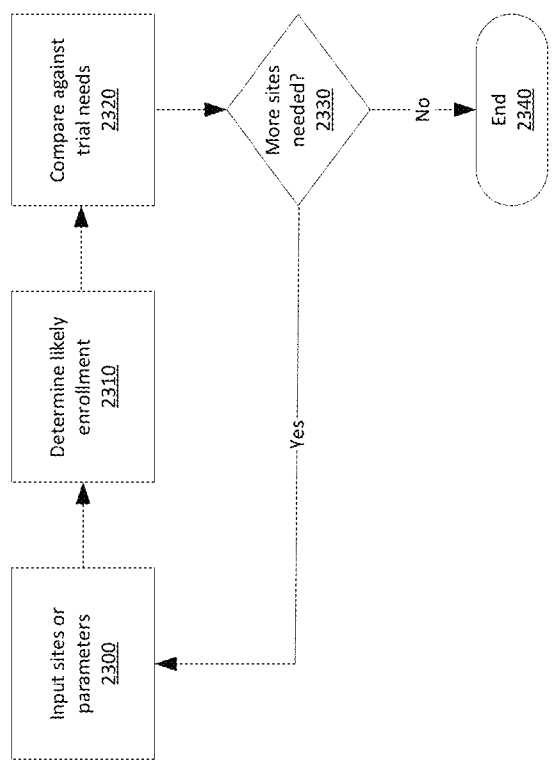
FIG. 23 is a flow chart illustrating site input according to one embodiment.

FIG. 23 is a flow chart illustrating site input according to one embodiment. In some embodiments, a user inputs one or more investigator sites and/or data parameters defining the enrollment needs for a clinical trial. Next, an algorithm determines the likely sum enrollment of all the selected investigator sites. Last, the sum enrollment is compared against the needs of a particular clinical trial to determine whether more or fewer investigator sites are needed to meet the parameters of the clinical trial.

Figure 24:
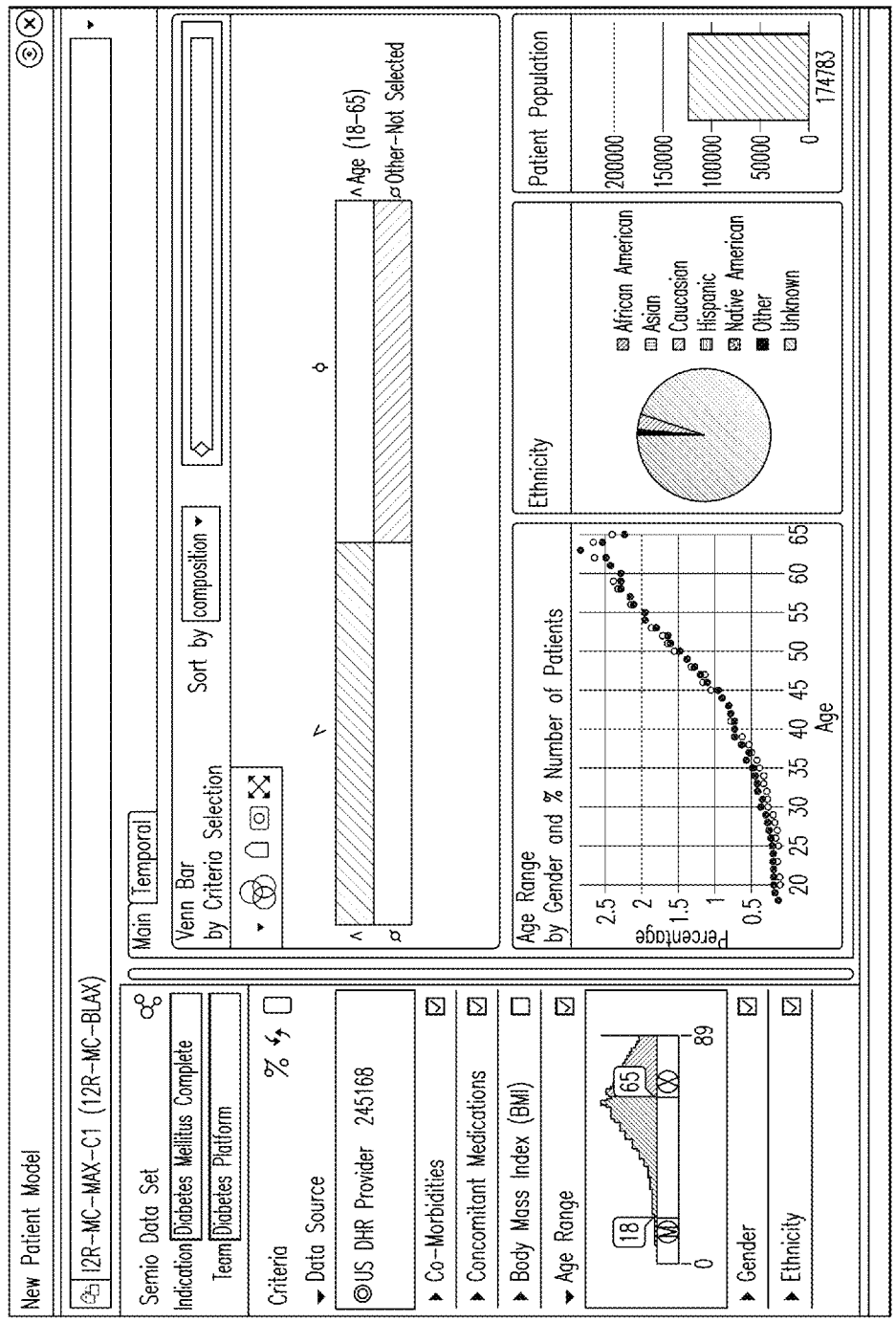
FIG. 24 is a diagram illustrating a patients editor according to one embodiment.

FIG. 24 is a diagram illustrating a patients editor according to one embodiment. In some embodiments, a patients editor comprises a means by which one or more users may enter information identifying optimal patient enrollment parameters. In some embodiments, such as the one illustrated in FIG. 24, a patients editor comprises sliders which users configure to set patient inclusion and exclusion limits within data categories. The data categories may include any relevant data, such as one or more of: co-morbidities, concomitant medications, body mass index, age, gender, and ethnicity. In some embodiments, a patients editor comprises graphs, tables, and other visual representations of data showing the number of patients included and excluded pursuant to user-defined criteria.

For example, in the embodiment illustrated in FIG. 24, a Venn Bar diagram represents the exclusion and inclusion parameters and shows the number of included and excluded patients due to particular selection criteria. Users can manipulate the sliders to arrive at a desired number of potential patients. Further, the patient editor may present graphs, such as line and/or pie graphs of various facets, such as age and ethnicity. Further, a bar graph of the patient population based on selected facet limits may be provided.

Figure 25:
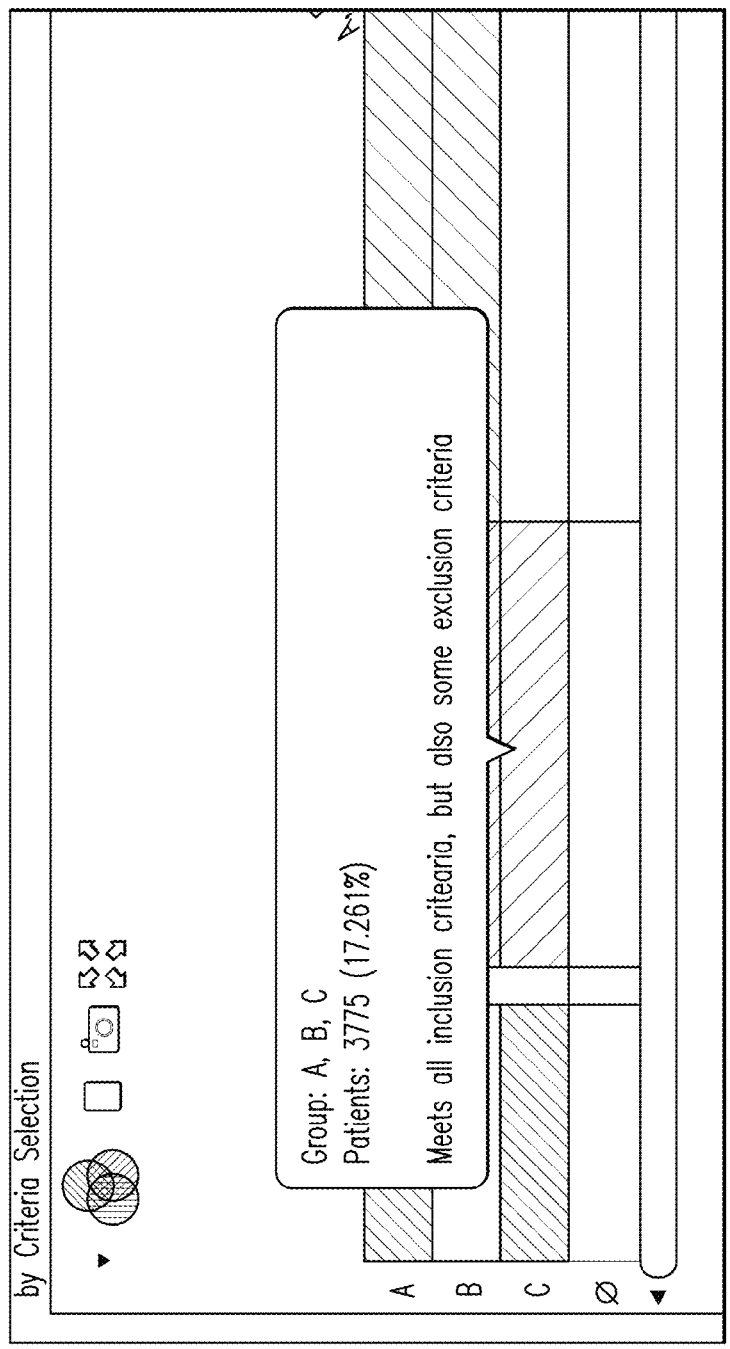
FIG. 25 is a diagram illustrating a patients editor according to one embodiment.

FIG. 25 is a diagram illustrating a patients editor according to one embodiment. Specifically, FIG. 25 depicts a portion of a Venn Bar diagram. In this illustrative embodiment, Venn fragment A represents age criteria, fragment B represents a history of cardiovascular disease, and fragment C represents the absence of opioid agonists. In some embodiments, upon selection of a fragment a popup window displays the number of patients represented by the fragment.

In some embodiments, a standard of care editor is provided. A standard of care editor comprises a means by which one or more users may select comparator drugs for trials. In some embodiments, a standard of care editor comprises graphs, tables, and other visual representations of data showing exemplary standards of care for one or more patients.

Figure 26:
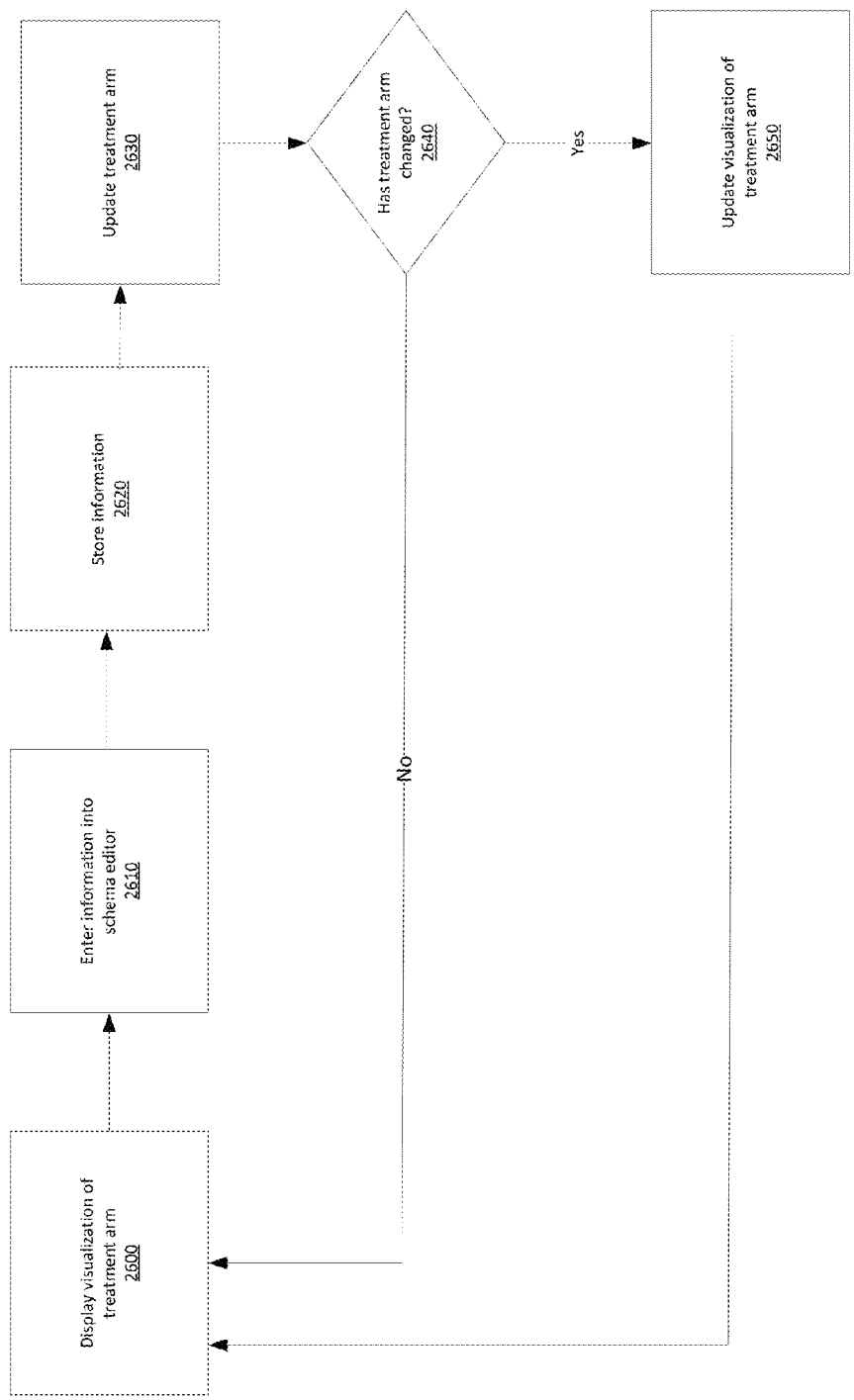
FIG. 26 is a flow chart illustrating use of a schema editor according to one embodiment.

FIG. 26 is a flow chart illustrating use of a schema editor according to one embodiment. As discussed herein, embodiments of the invention provide a schema editor. A user may enter information into the schema editor via the client 100, and the schema editor may be executed as one or more processes on one or more of the client 100, Application Server 200, and web server 300. Further, in some embodiments the schema editor accesses and/or updates information stored in the database 400.

Turning to FIG. 26, some embodiments display a visualization of a treatment arm 2600. As discussed herein, a treatment arm represents the treatment(s) to be provided to the patient(s) participating in the trial. An example of a visualization of a treatment arm is shown in FIG. 12.

Next, according to some embodiments, a user may enter information into the schema editor 2610. The information may include any information relevant to the schema of a trial. For example, the schema editor may allow the user to enter information about the patient population and the treatments they will receive—e.g., drug treatment(s), biopsy, blood test(s), questionnaires, and the like.

According to some embodiments, the information entered into the schema editor is stored 2620. For example, the information may be stored in the database 400. This illustrates a benefit of the present invention. In prior art systems, information about trial schemas was stored in a variety of documents, such as spreadsheets, word processing documents, and the like. While efforts were often made to keep such documents in a common repository, such as a shared network drive, there was not a single database of trial information. Thus, if information contained in one document was relevant to the subject matter of another document, a user was required to manually copy that information from one document to the other. This led to needless duplication of effort and increased the likelihood of errors in transcription. However, as shown herein, embodiments of the present invention store the information in a centralized location that can be accessed by the relevant processes. An effect of this is that a particular piece of information need only be entered one time, and after that it is available to other processes that need the information.

Next, according to some embodiments, the treatment arm is updated based on the information entered 2630. For example, if a user entered a particular drug regimen into the schema editor, the corresponding treatment arm is updated to include that drug regimen. This updating is done dynamically.

Next, according to some embodiments, a determination is made whether the treatment arm has changed 2640. If the treatment arm has not changed, then the visualization remains the same. If the treatment arm has changed, then the visualization of the treatment arm is updated to include the change 2650.

Embodiments of the invention may also include a schedule of events which provides information such as measurements, scales, and the like, based on the information entered into the schema editor. The schedule of events is dynamically generated from changes made to the schema. This illustrates a benefit of the present invention. In prior art systems, a user was required to make two changes—one to the schema and one to the schedule. However, embodiments of the present invention allow a user to make a change in one place (the schema editor) and the change is populated elsewhere (to the schedule of events). This has numerous benefits. For example, it saves duplicative labor. Also, it reduces the chance of error because under the prior art systems, a user could make a mistake while entering the information a second time.

Although many examples described in the present disclosure relate to clinical trial planning and design, it should be understood that the scope of the present disclosure is intended to encompass other applications where predictive clinical planning, design, and integrated execution services are used in research and development. Other advantages will become apparent to one of ordinary skill in the art from an understanding of the present disclosure.

The foregoing description of the embodiments of the invention has been presented only for the purpose of illustration and description and is not intended to be exhaustive or to limit the invention to the precise forms disclosed. Numerous modifications and adaptations are apparent to those skilled in the art without departing from the spirit and scope of the invention.

We claim:

1. A non-transitory computer-readable medium embodying computer program code for developing a plan for a clinical trial, the computer program code comprising computer executable instructions for:

receiving schema information for the clinical trial from a user interface, the schema information associated with one or more patients for the clinical trial, one or more investigators for the clinical trial, or enrollment criteria for the clinical trial;

generating a schema based at least in part on the schema information, the schema including at least one treatment arm and at least one visit structure for the clinical trial;

receiving patient burden information for the clinical trial, the patient burden information being associated with the at least one visit structure and comprising information about measures to be performed on or by a patient during one or more visits during the clinical trial;

calculating a burden score representing a burden imposed on the patient from participation in the clinical trial, the burden score calculated from the patient burden information;

generating a graphical representation of the schema and the burden score; and storing the schema and the burden score in a database.

2. The computer-readable medium of claim 1, wherein the schema information comprises treatment information for a patient population.

3. The computer-readable medium of claim 1, further comprising a graphical user interface.

4. The computer-readable medium of claim 1, further comprising computer program code comprising computer executable instructions for automatically updating a schedule of events based on at least a portion of the schema information.

5. The computer-readable medium of claim 1, further comprising computer program code comprising computer executable instructions for:

providing a schedule of events editor, wherein a schedule of events editor is configured to:

enable a user to designate which of the schema information will be obtained from a patient in a clinical trial on a particular visit; and determine a cost and the burden associated with obtaining the schema information.

6. The computer-readable medium of claim 5, wherein the schedule of events editor is configured to access at least a portion of the schema information.

7. A computer-implemented method comprising:

enabling a user to enter information regarding a clinical trial into a schema editor, wherein the information comprises patient information identifying parameters associated with one or more patients for the clinical trial, investigator information associated with one or more investigators for the clinical trial, or enrollment information associated with enrollment criteria for the clinical trial;

storing the information entered into the schema editor;

generating a schema based at least in part on the information entered into the schema editor, the schema including a treatment arm and a visit structure;

receiving patient burden information for the clinical trial, the patient burden information being associated with the visit structure and comprising information about measures to be performed on or by a patient during one or more visits during the clinical trial; and calculating a burden score representing a burden imposed on the patient from participation in the clinical trial, the burden score calculated from the patient burden information.

8. The computer-implemented method of claim 7, further comprising:

displaying a visualization of the schema and the burden score.

9. The computer-implemented method of claim 7, wherein the schema information comprises treatment information for a patient population.

10. The computer-implemented method of claim 7, wherein the schema editor comprises a graphical user interface.

11. The computer-implemented method of claim 7, further comprising automatically updating a schedule of events based on at least a portion of the schema information.

12. The computer-implemented method of claim 7, further comprising providing a schedule of events editor, wherein a schedule of events editor:

enables a user to designate which of the information will be obtained from a patient in a clinical trial on a particular visit; and determines a cost and the burden associated with obtaining the information.

* * * * *